(12) United States Patent
Mutharasan et al.

(10) Patent No.: US 7,892,759 B2
(45) Date of Patent: Feb. 22, 2011

(54) ENHANCED SENSITIVITY OF A CANTILEVER SENSOR VIA SPECIFIC BINDINGS

(75) Inventors: Rajakkannu Mutharasan, West Chester, PA (US); David R. Maraldo, Gilbertsville, PA (US); Kishan Rijal, Harleysville, PA (US); Gossett Augustus Campbell, Gilbertsville, PA (US); Paul Karl Horan, Kennett Square, PA (US)

(73) Assignees: Drexel University, Philadelphia, PA (US); Leversense, LLC, Newtown Square, PA (US)

(*) Notice: Subject to any disclaimer, the term of this patent is extended or adjusted under 35 U.S.C. 154(b) by 218 days.

(21) Appl. No.: 12/032,302

(22) Filed: Feb. 15, 2008

(65) Prior Publication Data

US 2009/0053709 A1 Feb. 26, 2009

Related U.S. Application Data

(60) Provisional application No. 60/890,370, filed on Feb. 16, 2007.

(51) Int. Cl.
| | |
|---|---|
| G01N 33/53 | (2006.01) |
| G01N 33/543 | (2006.01) |
| G01N 33/551 | (2006.01) |
| G01N 33/553 | (2006.01) |
| G01N 25/18 | (2006.01) |
| C12Q 1/00 | (2006.01) |
| C12M 1/34 | (2006.01) |
| C12M 3/00 | (2006.01) |
| G01N 21/00 | (2006.01) |
| G01N 31/22 | (2006.01) |
| G01N 15/06 | (2006.01) |
| G01N 33/00 | (2006.01) |
| G01N 33/48 | (2006.01) |
| G01N 27/00 | (2006.01) |
| H02K 44/00 | (2006.01) |

(52) U.S. Cl. ............ 435/7.1; 435/4; 435/287.1; 435/287.2; 436/518; 436/524; 436/525; 436/149; 422/57; 422/68.1; 422/82.01; 310/311

(58) Field of Classification Search ............... None
See application file for complete search history.

(56) References Cited

U.S. PATENT DOCUMENTS 4,483,929 A * 11/1984 Szoka ............... 436/533

(Continued)

FOREIGN PATENT DOCUMENTS

| EP | 0631319 A1 | 12/1994 |
|---|---|---|
| EP | 1536227 A2 | 6/2005 |
| WO | 98/50773 A2 | 11/1998 |
| WO | 2005/043126 A2 | 5/2005 |

OTHER PUBLICATIONS

Campbell, G.A., et al., "Method of Measuring *bacillus anthracis* spores in the presence of copious amounts of *bacillus thuringiensis* and *bacillus cereus*," Anal. Chem., published online Dec. 22, 2006, 79(3), 1145-1152.

(Continued)

*Primary Examiner*—Unsu Jung
*Assistant Examiner*—Leon Y. Lum
(74) *Attorney, Agent, or Firm*—Woodcock Washburn, LLP

(57) ABSTRACT

Detection of miniscule amounts of an analyte is accomplished via multiple bindings of specific materials on a sensor configured to sense mass. The sensor is prepared by immobilizing an antibody to a surface of the sensor, wherein the antibody is known to bind to the analyte. The prepared sensor is exposed to the analyte. The analyte binds to the antibody. The sensor then is exposed to additional antibody, which binds to the analyte. The sensor then can be sequentially exposed to additional antibodies that are known to bind to previously bound antibodies. Each additional binding further increases the effective mass of accumulated material on the sensor. The total effective mass is greater than the mass of the accumulated analyte, thus providing means for detecting extremely minute amounts of analyte. Applications include detection of pathogens and DNA.

22 Claims, 32 Drawing Sheets

U.S. PATENT DOCUMENTS

| | | | |
|---|---|---|---|
| 5,445,008 A | 8/1995 | Wachter et al. | 73/24.06 |
| 5,674,984 A * | 10/1997 | Berman et al. | 530/413 |
| 5,719,324 A | 2/1998 | Thundat et al. | 73/24.01 |
| 6,274,723 B1 | 8/2001 | Nilsen | 536/24.3 |
| 6,336,366 B1 | 1/2002 | Thundat et al. | 73/514.34 |
| 6,589,727 B1 | 7/2003 | Kleneman et al. | 435/4 |
| 6,630,309 B2 * | 10/2003 | Willner et al. | 435/7.1 |
| 7,195,909 B2 | 3/2007 | Kleneman et al. | 435/287.2 |
| 7,263,874 B2 | 9/2007 | Fitch et al. | 73/54.25 |
| 2003/0194697 A1 | 10/2003 | Kleneman et al. | 435/5 |
| 2003/0224551 A1 | 12/2003 | Kim et al. | 438/49 |
| 2005/0063882 A1 | 3/2005 | Centanni et al. | 422/292 |
| 2005/0164299 A1 | 7/2005 | Stewart | 435/7.1 |
| 2005/0229677 A1 | 10/2005 | Tuller et al. | 73/24.01 |
| 2005/0277852 A1 | 12/2005 | Shih et al. | 600/587 |
| 2006/0053870 A1 | 3/2006 | Berndt | 73/61.75 |
| 2006/0160098 A1 | 7/2006 | Zak et al. | 435/6 |
| 2006/0196253 A1 | 9/2006 | Crawley et al. | 73/53.01 |
| 2006/0223171 A1 | 10/2006 | Craighead et al. | 435/287.2 |
| 2006/0228657 A1 | 10/2006 | Masters et al. | 430/954 |
| 2007/0089515 A1 | 4/2007 | Shih et al. | 73/579 |
| 2007/0169553 A1 | 7/2007 | Mutharasan et al. | 73/579 |
| 2007/0218534 A1 | 9/2007 | Kleneman et al. | 435/173.7 |
| 2008/0034840 A1 | 2/2008 | Mutharasan et al. | 73/24.01 |
| 2008/0035180 A1 | 2/2008 | Mutharasan et al. | 134/32 |

OTHER PUBLICATIONS

Campbell, G.A., et al., "*Escherichia coli* O157:H7 detection limit of millimeter-sized PZT cantilever sensors in 700 cells/mL," Analytical Sci., Apr. 2005, 21, 11-13.

Campbell, G.A., et al., "Detection of pathogen *Escherichia coli* O157:H7 using self-excited PZT-glass microcantilevers," Biosensors and Bioelectronics, Sep. 15, 2005, Epub Dec. 21, 2004, 21(3), 462-473.

Campbell, G.A., "Detection of staphylococcus enterotoxin B at pictogram levels using piezoelectric-excited millimeter-sized cantilever sensors," Submitted on-line to J. of Analytical Chem, Mar. 29, 2006, 1-24.

Campbell, G.A., et al., "Detect of *Escherichia coli* O157:H7 in ground beef samples using piezoelectric excited millimeter-sized cantilever (PEMC) sensors," Biosens Bioelectron, Feb. 15, 2007, Epub Jul. 10, 2006, 22(7), 1296-1302.

Campbell, G.A., et al.,"A method of measuring *Escherichia coli* O157:H7 at 1 cell/mL in 1 liter sample using antibody functional piezoelectric-excited millimeter-sized cantilever sensor," Environ. Sci. Technol., published online Jan. 23, 2007, 41(5), 1668-1674.

Campbell, G.A., et al., "Detection and quantification of proteins using self-excited PZT-glass millimeter-sized cantilever," Biosensors and Bioelectronics, 2005, 21, 597-607.

Campbell, G.A., et al., "Piezoelectric-excited millimeter-sized cantilever (PEMC) sensors detect *Bacillus anthracis* at 300 spores/mL," Biosensors Bioelectronics, 2006, 21, 1684-1692.

Campbell, G.A., et al., "Detection of *bacillus anthracts* spores and a model protein using PEMC sensors in a flow cell at 1 mL/MIN," Biosens Bioelectron, Jul. 15, 2006, Epub Jan. 19, 2006, 22(1), 78-85.

Campbell, G.A., et al., "Detection of airborne *Bacillus anthracia* spores by an integrated system of an air sampler and a cantilever immunosensor," Sensors and Actuators B Chemical, Nov. 15, 2007, available online May 1, 2007, 127(2), 376-382.

Campbell, G.A., et al., "PEMC sensor's mass change sensitivity in 20 PG/HZ under liquid immersion," Biosensors and Bioelectronics, Jul. 15, 2006, Epub Jan. 18, 2006, 22(1), 35-41.

Campbell, G.A., et al., "Use of Piezoelectric-Excited Millimeter-Sized Cantilever Sensors to Measure Albumin Interaction with Self-Assembled Monolayers of Alkanethiols Having Different Functional Headgroups," Anal. Chem., available online Feb. 28, 2006, 78(7), 2328-2334.

Campbell, G.A., et al., "Detection of pathogen *Escherichia coli* O157:H7 using self-excited PZT-glass microcantilevers," Biosensors & Bioelectronics, Sep. 15, 2005, 21(3), 462-473.

Carr, D.W., et al., "Fabrication of nanoelectromechanical systems in single crystal silicon using silicon on insulator substrates and electron beam lithography," J. Vac. Sci. Technology, B, 15(6), 2760-2763 (1997).

Maraldo, D., et al., "Resonant-mode millimeter-sized cantilever biosensor for continuous detection of proteins and pathogens in flowing liquids," Dept. of Chem. And Biological Eng., 1-21, (submitted May 15, 2006 ).

Maraldo, D., et al., "Method for Quantification of a Prostate Cancer Biomarker in Urine without Sample Preparation," Analytical Chem., Available online Sep. 15, 2007, 79(20), 7683-7690.

Maraldo, D., et al., "Preparation-free method for detecting *Escherichia coli* O157:H7 in the presence of spinach, spring lettuce mix, and ground beef particulates," J. of Food protection, Nov. 2007, 70(11) 2651-2655.

Maraldo, D., et al., "Detection and confirmation of staphylococcal enterotoxin B in apple juice and milk using Piezoelectric-excited Millimeter-sized cantilever (PEMC) sensors at 2.5 femtograms/mL," Analytical Chem., 2007, 1-33.

Maraldo, D., et al., "Quantifying cancer biomarkers in body fluids: The case of AMACR in urine," Paper submitted to Proceedings of the Nat. Acad. of Sci., USA, Jan. 30, 2007, 1-39.

Maraldo, D., et al., "10-minute assay for detecting *escherichia coli* O157:H7 in ground beef samples using piezoelectric-excited millimeter-sized cantilever (PEMC) sensors," J. of Food Protection, 1-31, ( 2007 ).

Maraldo, D. et al., "Method for Label-Free Detection of Femtogram Quantities of Biologics in Flowing Liquid Samples," Anal. Chem., Apr. 1, 2007, 79(7), 2762-2770.

Rijal, K., et al., "PEMC-based method of measuring DNA hybridization at femtomolar concentration directly in human serum and in the presence of copious non-complementary strands," Analytical Chem., 2007, 34.

Rijal, K., et al., "A method for measuring self-assembly of alkanethiols on gold at femtomolar concentrations," Langmuir, 2006, 1-41.

Seung S. Lee, et al., "Self-excited piezoelectric cantilever oscillators," Transducers '95- Eurosensors IX, The 8th Int. Conf. on Solid-State Sensors and Actuators, and Eurosensors IX, Stockholm, Sweden, Jun. 25-29, 1995, 417-420.

Wilson, L., et al., "Viscosity and density values from excitation level response of piezoelectric-excited cantilever sensors," Sensors and Actuators A, Jul. 20, 2007, 138, 44-51.

Wilson, L., et al., "Piezoelectric-excited millimeter-sized cantilever (PEMC) sensor provides viscosity and density measurements," Submitted to Review of Scientific Instruments, May 30, 2005, 1-26.

Yi Jeong W. et al., "In situ cell detection using piezoelectric lead zirconate titanate-stainless steel cantilevers," J Applied Physics, Jan. 1, 2003, 93(1), 619-625.

Zhou J. et al., "Zeolite-modified microcantilever gas sensor for indoor air quality control," Sensors and Actuators B, Oct. 1, 2003, 94(3), 337-342.

U.S. Appl. No. 11/747,183 by Mutharasan, et al., filed May 10, 2007.
U.S. Appl. No. 12/130,446 by Mutharasan, et al., filed May 30, 2008.
U.S. Appl. No. 12/141,846 by Mutharasan, et al., filed Jun. 18, 2008.
U.S. Appl. No. 60/746,948 by Mutharasan, filed May 10, 2006.
U.S. Appl. No. 60/746,951 by Mutharasan, et al., filed May 10, 2006.
U.S. Appl. No. 60/807,020 by Mutharasan, et al., filed Jul. 11, 2006.
U.S. Appl. No. 60/944,592 by Mutharasan, filed Jun. 18, 2007.
U.S. Appl. No. 60/954,488 by Mutharasan, filed Aug. 7, 2007.

* cited by examiner

SEQUENCE LISTING

```
<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
ctccagggcc aggcggcg                                                   18

<210> SEQ ID NO 2
<211> LENGTH: 288
<212> TYPE: DNA
<213> ORGANISM: Artificial Sequence
<220> FEATURE:
<223> OTHER INFORMATION: Primer

<400> SEQUENCE: 2
catttccagg agaaagtgga atctttggaa caggaagcag ccaacgagag acagcagctg     60
gtggagacac acatggccag agtggaagcc atgctcaatg accgccgccg cctggccctg   120
gagaactaca tcaccgctct gcaggctgtt cctcctcggc ctcgtcacgt gttcaatatg   180
ctaaagaagt atgtccgcgc agaacagaag gacagacagc acaccctaaa gcatttcgag   240
catgtgcgca tggtggatcc caagaaagcc gctcagatcc ggtcccag                288

<210> SEQ ID NO 3
<211> LENGTH: 18
<212> TYPE: DNA
```

-continued

```
<213> ORGANISM: Artificial Sequence
<220> FEATURE:
<223> OTHER INFORMATION: Primer

<400> SEQUENCE: 3
cgccgcctgg ccctggag                                                  18

<210> SEQ ID NO 4
<211> LENGTH: 35
<212> TYPE: DNA
<213> ORGANISM: Artificial Sequence
<220> FEATURE:
<223> OTHER INFORMATION: Primer

<400> SEQUENCE: 4
aatgaccgcc gccgcctggc cctggagaac tacat                               35

<210> SEQ ID NO 5
<211> LENGTH: 18
<212> TYPE: DNA
<213> ORGANISM: Artificial Sequence
<220> FEATURE:
<223> OTHER INFORMATION: Reverse Primer

<400> SEQUENCE: 5
ctccagggcc aggcggcg                                                  18
```

ENHANCED SENSITIVITY OF A CANTILEVER SENSOR VIA SPECIFIC BINDINGS

CROSS REFERENCE TO RELATED APPLICATIONS

The present application claims priority to U.S. Provisional Patent Application No. 60/890,370, entitled "ENHANCED SENSITIVITY OF A SELF-EXCITED PIEZOELECTRIC CANTILEVER SENSOR VIA ADDITIONAL ANTIBODY BINDING," filed Feb. 16, 2007, which is hereby incorporated by reference in its entirety.

TECHNICAL FIELD

The technical field generally relates to the detection of materials in a liquid or gas media. More particularly, the technical field relates to the use of a cantilever sensor to provide very sensitive detection of materials in liquid or gas media via binding of specific materials.

BACKGROUND

Pathogens can be dangerous to the public. For example, Enterohemorrahagic *Escherichia coli* O157:H7 (*E. coli* O157:H7), a foodborne pathogen, is a facultative gram-negative *bacillus* that is dangerous and has been implicated in outbreaks of illness due to ingestion of meats, water, and uncooked fruits and vegetables. *E. coli* O157:H7 is cable of producing a variety of human illnesses which include hemolytic uremic syndrome and diarrhea. The outbreaks of *E. coli* O157:H7 food poisoning in the US over the past few decades and the sporadic worldwide outbreaks caused by contaminated ground beef has raised growing interest in rapid pathogen identification.

Current methods for detecting foodborne pathogens are time consuming and not very sensitive. Traditionally, detection of foodborne pathogens has involved sample collection, enrichment, followed by isolation and identification of the targeted organism by a variety of methods. The current methods capable of foodborne pathogen detection include traditional enrichment and plating methods in selective media, polymerase chain reaction (PCR), fiber optic biosensors, immuno-magnetic beads, and quartz crystal microbalance (QCM). Each of the stated methods has its own set of limitations. Enrichment and plating approach lack sensitivity and specificity, and often takes 24-96 hours to identify the contaminant organism. Most immuno-magnetic assays and fiber optic biosensors require pre-enrichment of the sample since the pathogenic bacteria is present in concentrations below the technology's limit of detection. In addition to sample enrichment requirements, PCR methods have a higher cost, and require well-trained personnel. QCM analysis is not very sensitive and, therefore its use is limited when EC is present at high concentration with a high level of contaminants. In addition to the individual limitations, the current methods of food sampling do not ensure 100% absence of unwanted, potentially cross-reactive, contaminants due to the intrinsic nature of sample collection.

SUMMARY

Cantilever sensors, such as piezoelectric cantilever sensors, bending mode cantilever sensors, QCM cantilever sensors, or the like, are used to detect pathogens via binding of additional specific materials (e.g., antibodies) to the sensor and to materials accumulated on the sensor. The specific materials are not labeled. A sensor is prepared by immobilizing an antibody or the like on a cantilever surface of the sensor. The immobilized antibody is known to bind (bindable) to a target analyte, such as an antigen, pathogen, or the like. The prepared sensor is exposed to the target analyte. The target analyte binds to the antibody immobilized on the surface of the cantilever sensor, resulting in an increase in effective mass of the cantilever sensor. The cantilever sensor responds to changes in mass that occur due to binding of target molecules to the sensor surface, as observed via a corresponding change in resonance frequency of the sensor. The sensor is then exposed to additional antibodies that bind to the target analyte that has accumulated on the cantilever surface. The accumulation of additional antibodies further increases the effective mass of the cantilever, which results in a further change in resonance frequency. Additionally, the change in resonance frequency over time reflects the kinetics of the binding reaction between recognition molecules and analytes, and recognition molecules and recognition molecules. The rate at which the binding reactions reach equilibrium is utilizable to quantify the affinity of the binding partners for one another, which in turn facilitates identification of binding partners. In various example embodiments, the sensor is exposed to more antibodies known to bind to the previously exposed antibodies, thus causing even further change in effective mass of the sensor. Monitoring the resonance frequency change provides quantitative measures of the target analyte in the sample.

BRIEF DESCRIPTION OF THE DRAWINGS

The foregoing summary, as well as the following detailed description, is better understood when read in conjunction with the appended drawings. For the purpose of illustrating enhanced sensitivity of a cantilever sensor via a plurality of specific bindings, there is shown in the drawings exemplary constructions thereof; however, enhanced sensitivity of a cantilever sensor via a plurality of specific bindings is not limited to the specific methods and instrumentalities disclosed.

DETAILED DESCRIPTION OF ILLUSTRATIVE EMBODIMENTS

As described herein, the ability to detect incredibly small changes in mass of a target analyte is achieved via the use of a piezoelectric-excited cantilever sensor and binding of recognition molecules as described herein. Recognition molecules can comprise any appropriate recognition molecules such as an antibodies and/or fragments thereof, antigens, receptors or portions thereof, agonists, antagonists, peptides, proteins, carbohydrates, glycoproteins, lipids, phospholipids, or dendrimers which display a high specificity and affinity or avidity to bind a specific analyte, DNA, RNA, or the like. Antibodies can comprise monoclonal antibodies which bind to the target analyte via single binding sites, polyclonal antibodies which bond to the target analyte via multiple binding sites, or any combination thereof. Dendrimers can comprise highly branched molecules that are constructed from interconnecting natural or synthetic monomeric units, e.g., single stranded DNA or RNA, partially denatured double stranded DNA, proteins, such as antibodies, having a DNA or RNA strand attached to it. The highly branched structure can be built through sequential series of hybridization reactions in which monomeric units hybridize to complementary strands. The monomeric units may be labeled with dyes, metals, enzymes, or radioactivity to increase the mass and facilitate detection when bound. The recognition molecules can include unlabeled reagents and/or labeled reagents. A labeled reagent could include any appropriate labeled reagent, such as for example, an antibody with a particle such as metal, latex, or the like. Analytes can comprise any appropriate analyte target material, such as for example, a specific protein, carbohydrate, glycoprotein, protein complex, DNA molecule, cDNA molecule, cRNA molecule, RNA molecule, RNAi molecule, pRNA molecule, mycoplasma, virus, bacterium, yeast, mammalian cell, prions, or phospholipid.

Although detection of a target analyte via binding of recognition molecules is described herein with respect to piezoelectric cantilever sensors, it is to be understood however, that any appropriate sensor can be utilized, and that the herein described processes and techniques are not limited to only piezoelectric cantilever sensors. For example, the herein described processes and techniques are applicable to bending mode cantilever sensors and QCM sensors. In an example embodiment, selectivity to a specific analyte is achieved by immobilizing recognition molecules to the sensor. The recognition molecules are known to bind (bindable) to a target material.

Figure 1:
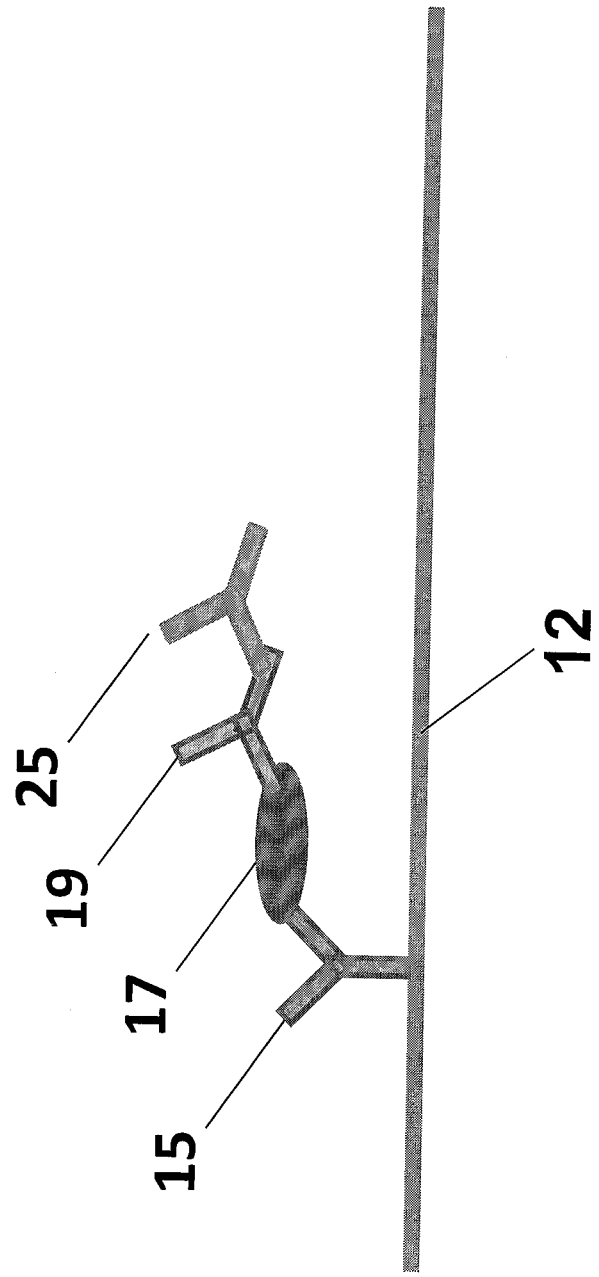
FIG. 1 is a diagram of an example antibody ladder accumulated on a mass sensing sensor surface.

FIG. 1 is a diagram of an example antibody ladder accumulated on a mass sensing sensor surface 12. The antibody ladder comprises an antibody 15 that has been immobilized on the sensor surface 12. An antibody 15 (also referred to herein as a recognition molecule(s)) is bound to an analyte 17. In an example embodiment, the antibody 15 is known to be attracted to (bindable) to the analyte 17. The analyte 17 is bound to an antibody 19. In an example embodiment, the antibody 19 is known to be attracted to (bindable) to the analyte 17. The antibody 19 may, or may not, comprise the same type antibody as antibody 15. The antibody 19 is bound to an antibody 25. In an example embodiment, the antibody 19 is known to be attracted to (bindable) to the antibody 25. The number of antibodies depicted in FIG. 1 is exemplary, and more or less antibodies can be bound in the ladder. Each antibody bound in the ladder contributes some amount of mass. Thus the mass sensing sensor will sense the effective mass of the ladder accumulated on the sensor surface 12, rather than only the mass of the analyte 17 accumulated on the sensor surface 12. The effect mass of the antibody ladder is greater than the mass of the analyte and thus detection performance is increased.

Figure 2:
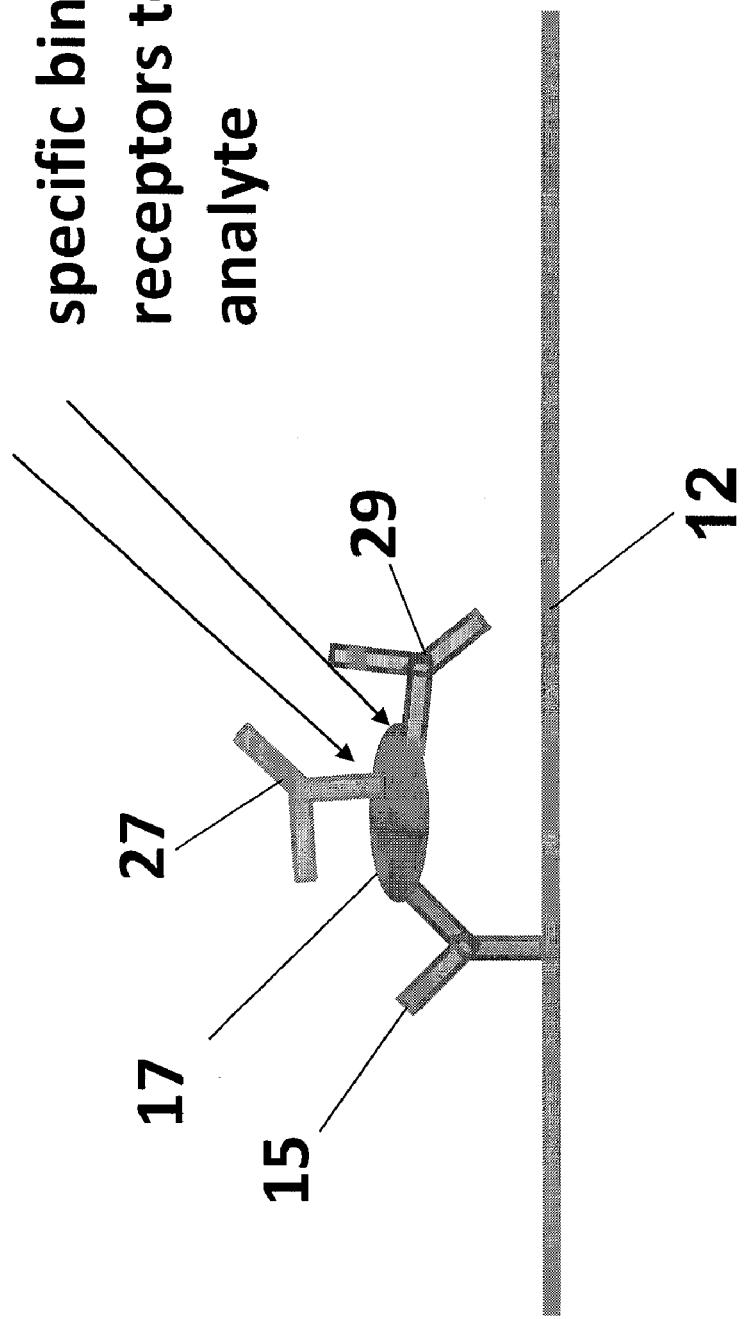
FIG. 2 is an example diagram of multiple antibodies bound to an analyte at different binding sites.

FIG. 2 is an example diagram of multiple antibodies 27, 29 bound to the analyte 17 at different binding sites. Multiple types of antibodies can be bound to the analyte 17 to increase the effective mass of material accumulated on the sensor surface 12. Any appropriate number of antibodies can be bound to the analyte 17. As is to be understood, each of the antibodies bound to the analyte 17 can have antibodies attached respectively thereto. Thus, the antibody 27 can have one or more antibodies bound thereto, and/or the antibody 29 can have one or more antibodies bound thereto. Additional antibodies increases the effective mass accumulated on the sensor surface 12 and thus improve detection performance.

Figure 3:
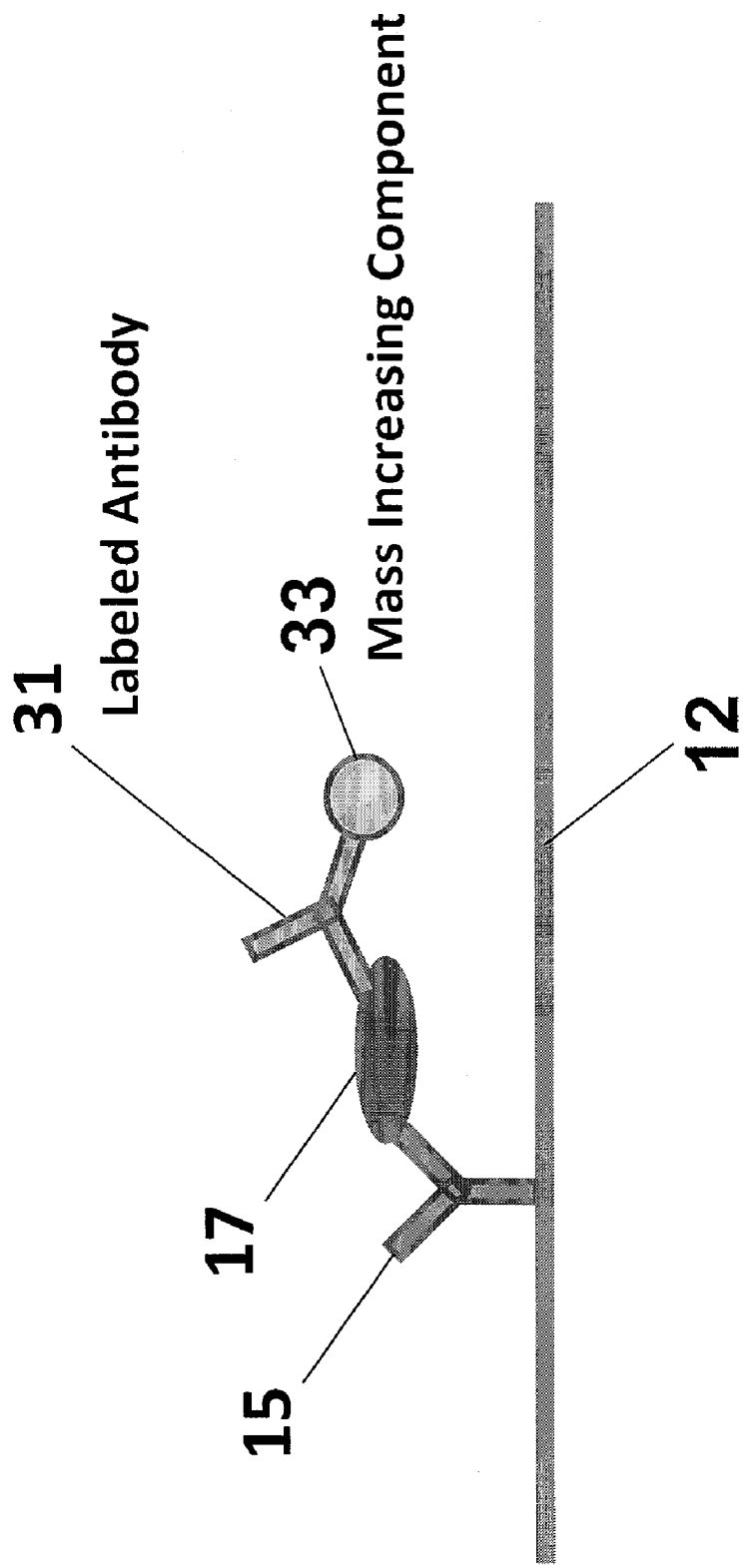
FIG. 3 is an example diagram of a labeled antibody bound to an analyte.

FIG. 3 is an example diagram of a labeled antibody 31 bound to the analyte 17. The antibodies used to bind to the analyte can be unlabeled, labeled as depicted in FIG. 3, or a combination thereof. The labeled antibody 31 can comprise any appropriate labeled antibody. The label can comprise any appropriate mass increasing component 33 that can increase the effective mass of material accumulated on the sensor surface 12. For example, the labeled antibody 31 can comprise a conjugate with a heavy particle such as metal, latex, or the like. Each labeled antibody can comprise any appropriate number and type of mass increasing components. Any appropriate number of labeled antibodies and/or unlabeled antibodies can be bound to the analyte 17. In an example embodiment, the mass increasing component 33 may be a dendrimer.

Figure 4:
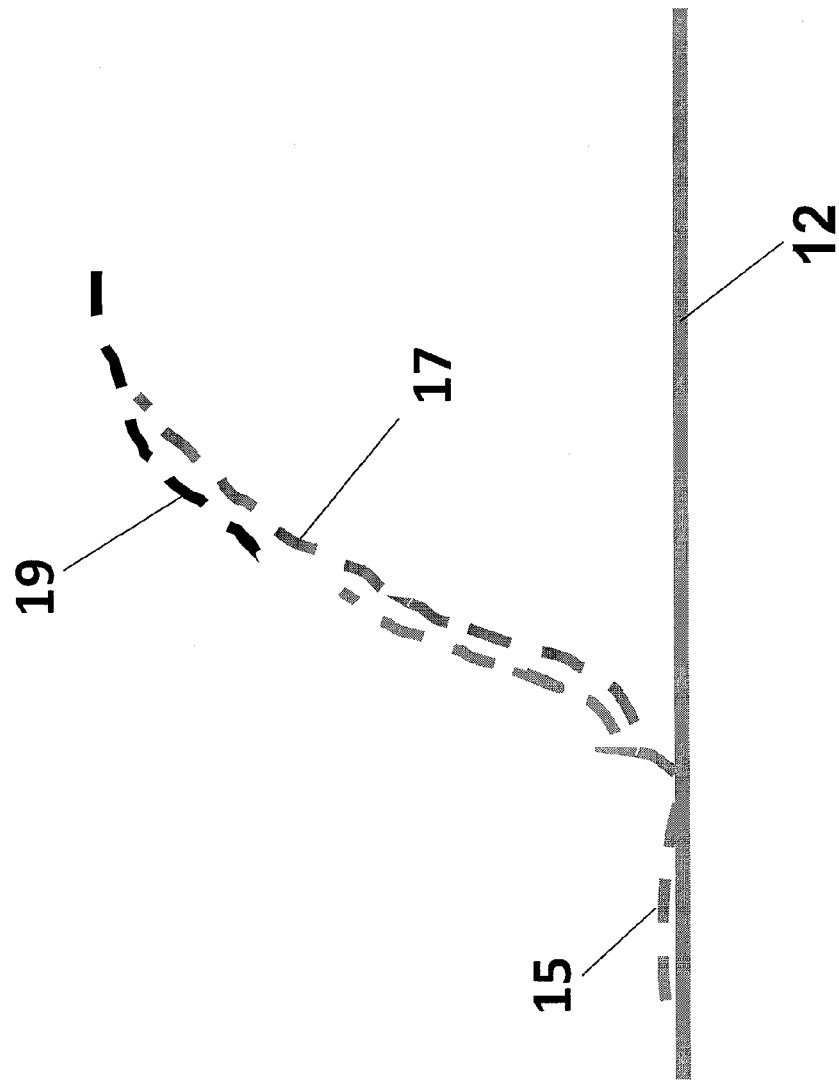
FIG. 4 is an example diagram illustrating an antigen ladder comprising DNA.

In an example embodiment, the recognition molecules and analyte comprise DNA and/or RNA. For the sake of simplicity, the following descriptions are with respect to DNA. FIG. 4 is an example diagram illustrating an antigen ladder comprising DNA. As depicted in FIG. 4 the recognition molecule 15 comprises a DNA antibody strand immobilized on the sensor surface 12. The analyte 17 comprises a complementary strand of DNA bound to the DNA strand 15. The analyte DNA 17 is bound to additional antibody DNA strand 19. The additional DNA strand 19 can be used to increase the effective mass accumulated on the sensor surface 12. The DNA strand 19 can be bound to the analyte DNA strand 17 via non-specific segments. The additional DNA strand 19 can be used to identify the analyte 17. In this case, the DNA strand 19 could be bound to specific receptor sites of the analyte DNA strand 17. As depicted in FIG. 4, the additional antibody DNA strand 19 is unlabeled.

Figure 5:
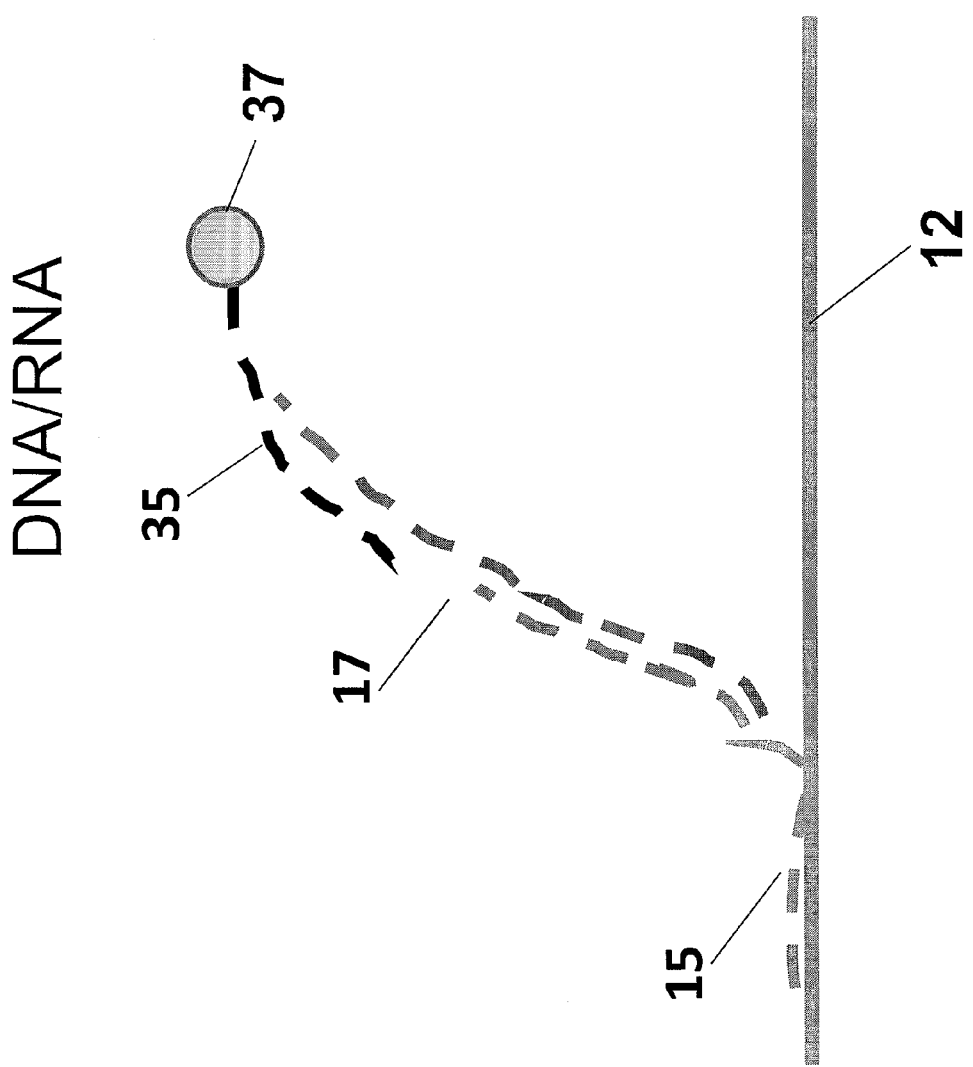
FIG. 5 is an example diagram illustrating an antigen ladder comprising labeled DNA.

FIG. 5 is an example diagram illustrating an antigen ladder comprising labeled DNA 35 comprising mass increasing entity 33. The labeled DNA strand 35 can comprise any appropriate labeled DNA strand. The label can comprise any appropriate mass increasing component 37 that can increase the effective mass of material accumulated on the sensor surface 12. For example, the labeled DNA strand 33 can comprise a conjugate with a heavy particle 37. Any appropriate number of labeled DNA strands and/or unlabeled DNA strands can be bound to the analyte 17. In an example embodiment, the mass increasing component 33 may be a dendrimer.

Figure 6:
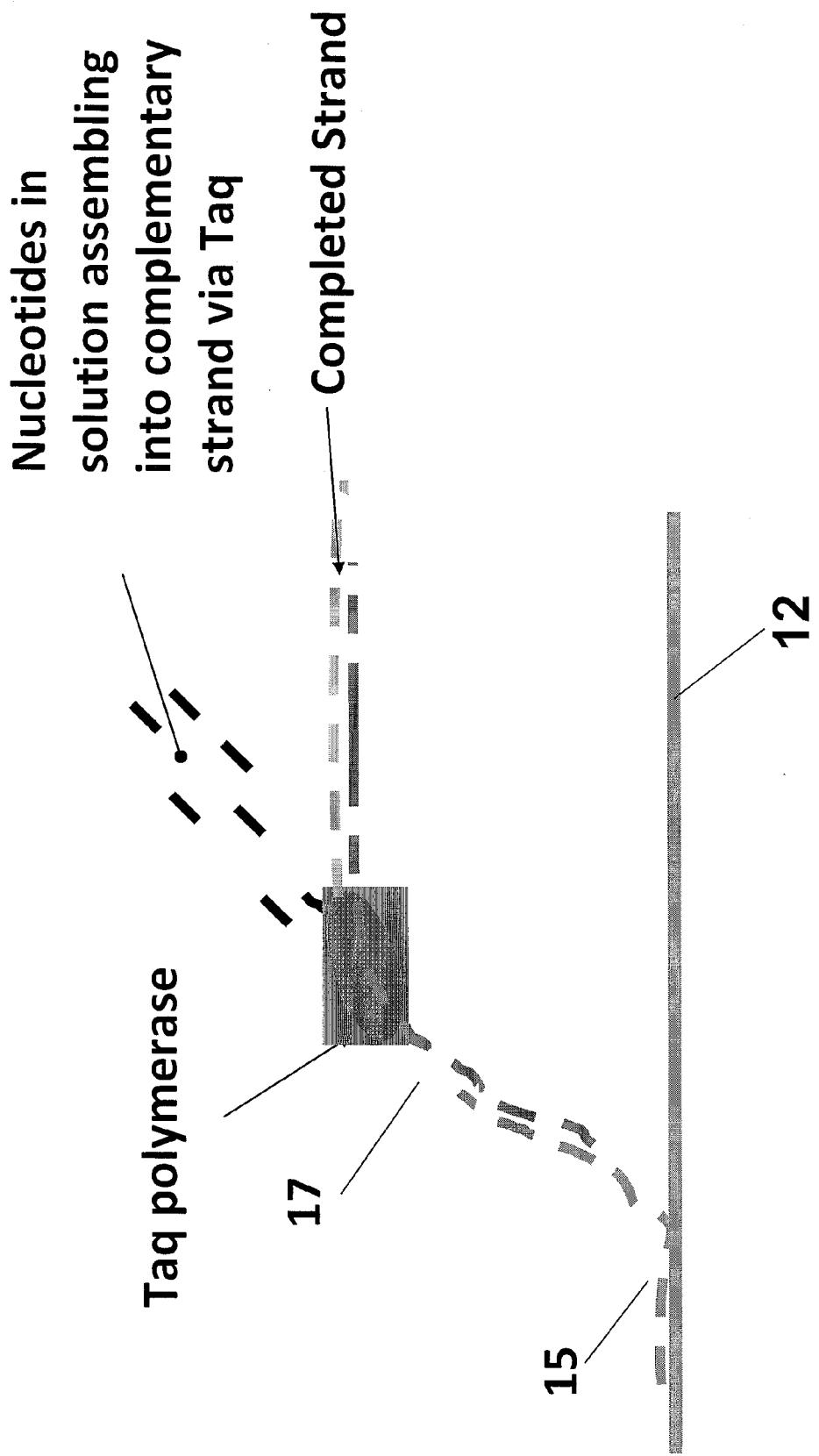
FIG. 6 illustrates using Taq polymerase as a reagent to facilitate the assembly of complementary strands of DNA and/or RNA.

In an example embodiment, as depicted in FIG. 6, Taq polymerase can be utilized as a reagent to facilitate the assembly of complementary strands of DNA and/or RNA. The Taq polymerase can be used to assemble a complementary strand of the analyte 17 in situ. Although Taq polymerase is depicted in FIG. 6, any appropriate polymerase can be utilized to facilitate the binding (assembly) of the analyte to an antibody.

Figure 7:
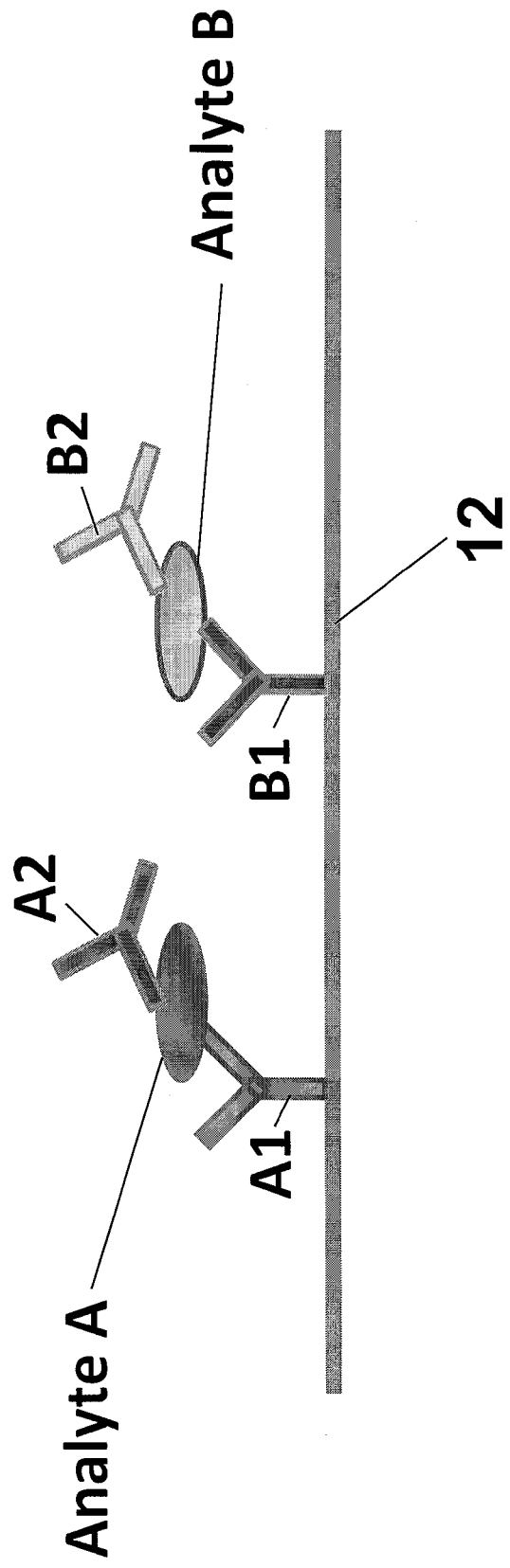
FIG. 7 is an illustration of multiple antibody bindings on a sensor surface.

Multiple types of antibodies, depicted as A1 and B1 in FIG. 7, can be immobilized on the surface of the sensor surface 12. Each type of immobilized antibody A1, A2 can be part of a respective ladder as described above. As depicted in FIG. 7, one ladder comprises antibody A1, analyte A, and additional antibody A2. The other ladder comprises antibody B1, analyte B, and additional antibody B2. Each ladder can be generated sequentially. Utilizing the multiple ladder scheme depicted in FIG. 7 allows the addition of additional antibodies without rinsing between additions. Thus, analyte A can be searched for and a decision made. Then, without rinsing the sensor surface 12, analyte B can be searched for a decision made. Further, the multiple ladder scheme can be applied to RNA and/or DNA with specificity and a variety of probes.

Figure 8:
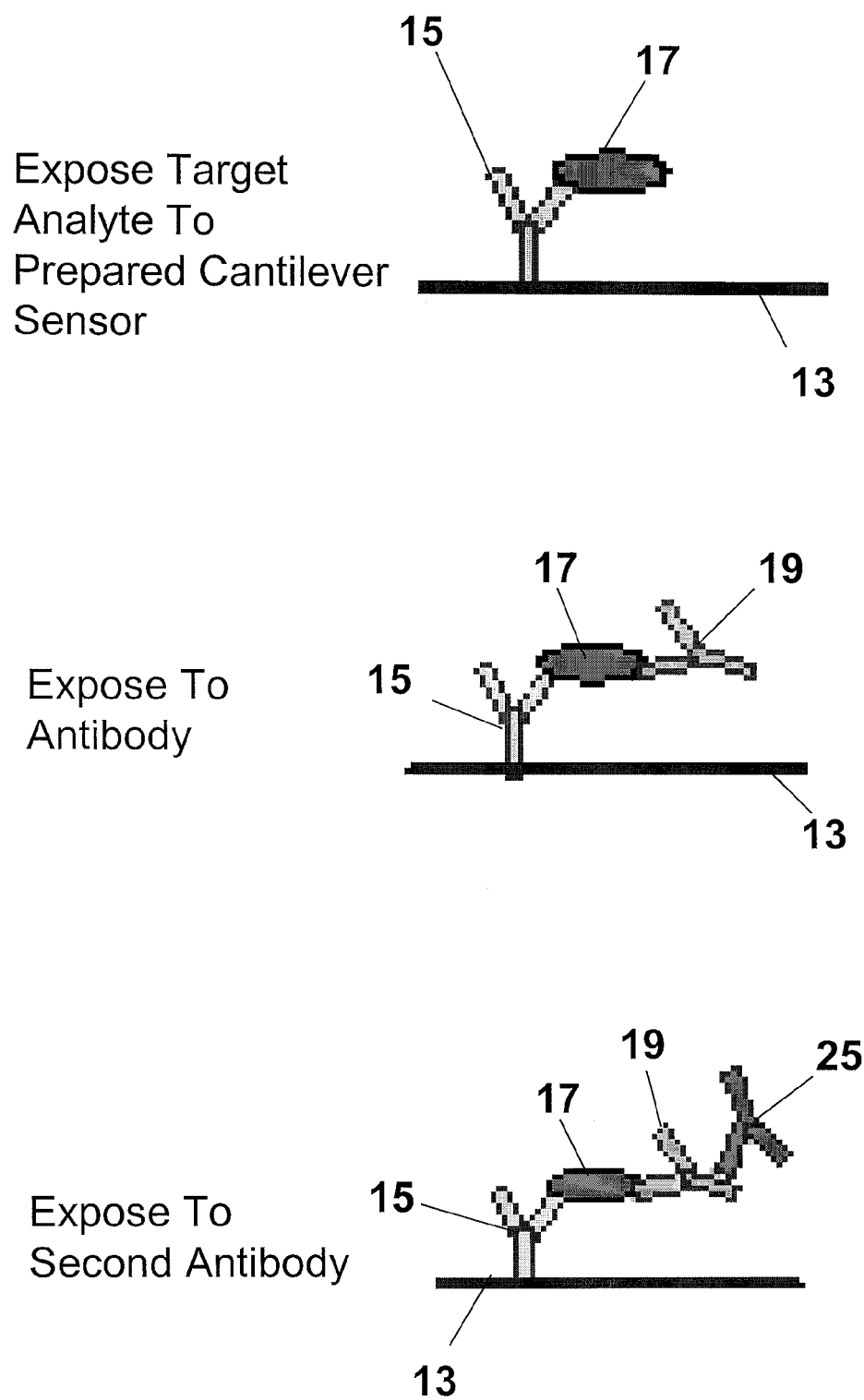
FIG. 8, is an illustration of an example process for using a cantilever sensor with additional specific bindings.

Referring to FIG. 8, which is an illustration of an example process for using a cantilever sensor with additional specific bindings, a cantilever sensor 13 is prepared by immobilizing an antibody 15 on the cantilever sensor 13. The prepared cantilever sensor 13 is exposed to a medium (e.g., fluid: liquid and/or gas) potentially containing a target analyte 17, such as a target antigen or the like. Assuming the target analyte 17 is contained in the medium, the target analyte 17 in the medium attaches to the antibody 15 on the piezoelectric cantilever sensor 13. The cantilever sensor 13, having the target analyte 17 attached thereto, is then exposed to a medium containing additional antibodies 19. The additional antibodies 19 attach to the target analyte 17 on the cantilever sensor 13. In an example embodiment, multiple antibody bindings are utilized to increase the effect mass of the cantilever sensor. For example, the cantilever sensor 13 is exposed to a second type of antibody 25 known to be attachable to the first antibody 19. The binding of the second type of antibody 25 increases the mass of accumulated material on the cantilever sensor 13 even further. The process can be continued by, for example, exposing the sensor to additional antibodies that are known to bind (bindable) to previously bond antibodies. For example, the sensor can be exposed to antibodies that are known to bind to the antibodies 25, and then exposing the sensor to antibodies to the previously attached antibodies, etc. Note that antibodies can be labeled or unlabeled. Thus, in the case of unlabeled antibodies, detection is accomplished without the use of primers or labeled reagents.

Example Sensor Overview

An example piezoelectric cantilever sensor comprises a piezoelectric layer acting as an actuating and a sensing element, and a borosilicate glass surface for antibody attachment. In an example configuration, piezoelectric lead zirconate titanate (PZT) substrates are utilized to provide sensitive responses to small stresses due to the direct piezoelectric effect, and the generation of high strain via the inverse piezoelectric phenomena. Millimeter-sized piezoelectric cantilever sensors are described in some applications herein as applied to enhanced sensitivity of a self-excited piezoelectric cantilever sensor via additional antibody binding, but are not limited thereto. Smaller sized (e.g., micro/nano sized) piezoelectric cantilever sensors are applicable to achieve enhanced sensitivity of a self-excited piezoelectric cantilever sensor via additional antibody binding. In example configurations, piezoelectric-excited millimeter-sized cantilever (PEMC)

sensors use the direct piezoelectric effect to excite the cantilever, and the same PZT film is used to sense the response. When an electric field is applied across the thickness of the PZT film, it extends along its length causing the base glass cantilever to bend. If the applied field is alternated periodically, the composite cantilever vibrates. The natural frequency of the cantilever depends on the flexural modulus and the mass density of the composite cantilever. At resonance, the cantilever undergoes significantly higher stresses when the exciting electric field is at resonance frequency. Hence, the PZT layer exhibits a sharp change in electrical impedance, and the resonance state can be followed by the phase angle.

Figure 9:
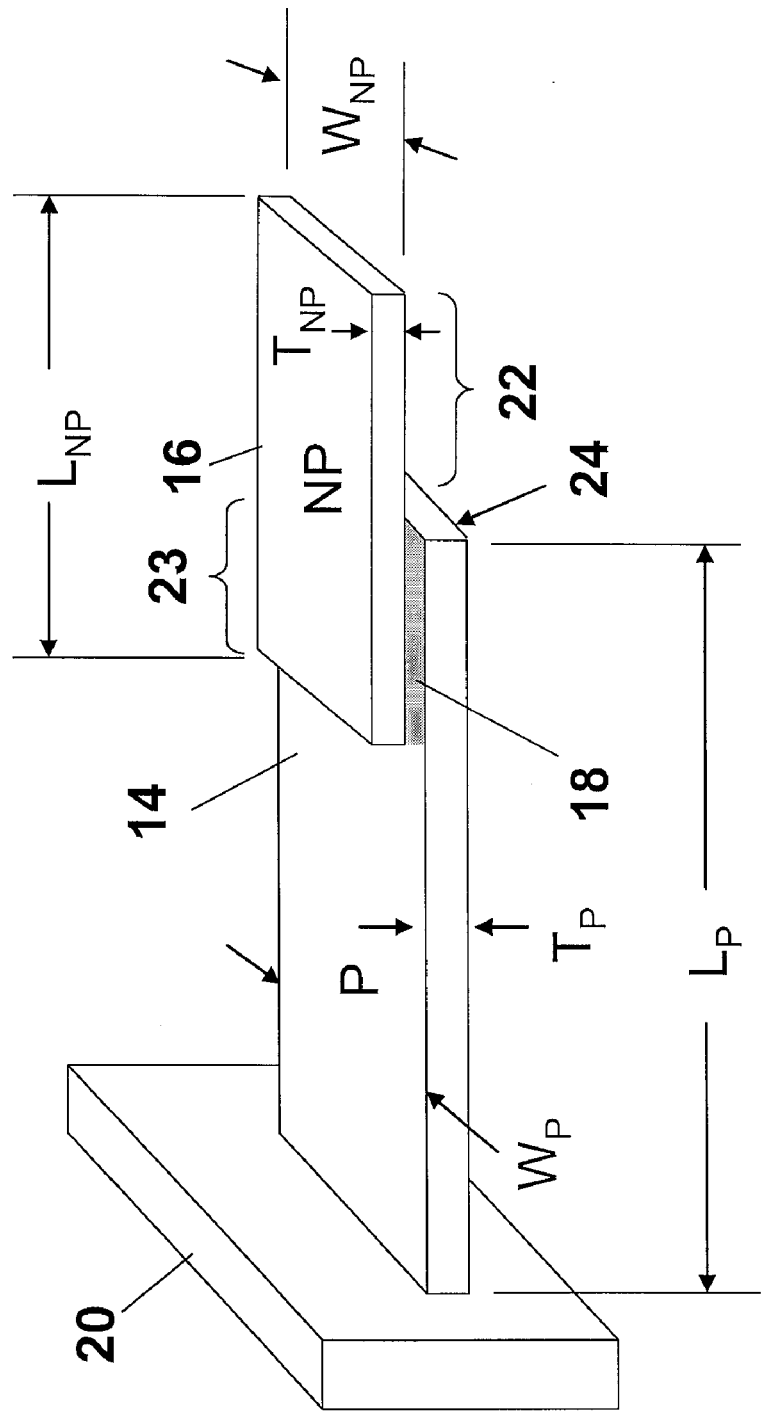
FIG. 9 is an illustration of an example configuration of a piezoelectric cantilever sensor.

FIG. 9 is an illustration of an example piezoelectric cantilever sensor 12. A piezoelectric cantilever sensor is described herein to provide an understanding of detecting a target analyte via additional binding of specific material. It is to be understood however, that other cantilever sensors are applicable, such as for example, bending mode cantilever sensors and QCM sensors.

The piezoelectric cantilever sensor 12 comprises a piezoelectric portion 14 and a non-piezoelectric portion 16. Piezoelectric portions are labeled with an uppercase letter p ("P"), and non-piezoelectric portions are labeled with the uppercase letters np ("NP"). The piezoelectric cantilever sensor 12 depicts an embodiment of an unanchored, overhang, piezoelectric cantilever sensor. The piezoelectric cantilever sensor 12 is termed "unanchored" because the non-piezoelectric layer 16 is not attached to the base portion 20. The piezoelectric cantilever sensor 12 is termed, "overhang" because the non-piezoelectric layer 16 extends beyond the distal tip 24 of the piezoelectric layer 14 to create an overhanging portion 22 of the non-piezoelectric layer 16. The piezoelectric portion 14 is coupled to the non-piezoelectric portion 16 via adhesive portion 18. The piezoelectric portion 14 and the non-piezoelectric portion overlap at region 23. The adhesive portion 18 is positioned between the overlapping portions of the piezoelectric portion 14 and the non-piezoelectric portion 16. The piezoelectric portion 14 is coupled to a base portion 20.

The piezoelectric cantilever sensor 12 provides the ability to detect and measure extremely small amounts of an analyte. The piezoelectric cantilever sensor 12 can be utilized to detect and measure an analyte immersed in a liquid and an analyte contained in a gas or vacuum. In various example configurations, the piezoelectric cantilever sensor 12 comprises at least one piezoelectric layer 14 and at least one non-piezoelectric layer 16, wherein the piezoelectric layer 14 is coupled to the non-piezoelectric layer 16. The piezoelectric layer 14, the non-piezoelectric layer 16, or both can be coupled to at least one base 20. The piezoelectric layer and the non-piezoelectric layer can be of varying widths ($W_P$), lengths ($L_P$, $L_{NP}$), and thicknesses ($T_P$, $T_{NP}$).

The piezoelectric cantilever sensor 12 is utilizable to determine the mass of an analyte accumulated thereon. In an example embodiment, a portion of the piezoelectric cantilever sensor is placed in a medium (e.g., liquid, gas, vacuum). While in the medium, a resonance frequency of the piezoelectric cantilever sensor is measured and compared to a baseline resonance frequency. The difference in the measured resonance frequency and the baseline resonance frequency is indicative of an amount of mass of analyte accumulated (e.g., bound, adsorbed, absorbed) on the piezoelectric cantilever sensor.

Analytes can be directly or indirectly bound to the surface of the non-piezoelectric portion 16 of the piezoelectric cantilever sensor 12. Binding of an analyte to the non-piezoelectric portion 16 of the piezoelectric cantilever sensor 12 results in a change in mass of the piezoelectric cantilever sensor 12. The changes in mass and/or stiffness are measurable as changes in resonance frequency, and can be monitored and measured by an appropriate analysis device, such as an operational amplifier, an impedance analyzer, a network analyzer, an oscillator circuit, or the like, for example. Resonance frequency changes, wherein at least a portion of the piezoelectric cantilever sensor 12 is immersed in a liquid, are detectable and measurable. Resonance frequency changes, wherein at least a portion of the piezoelectric cantilever sensor is immersed in a gas or a vacuum, also are detectable and measurable.

The piezoelectric cantilever sensor 12 is operateable at high frequencies, such as, on the order of 0.1 MHz. to 6 MHz, for example. At these high frequencies, a Q factor (the ratio of the resonance peak frequency relative to the resonance peak width at half peak height), on the order of 10 to 100, under liquid immersion is obtainable. The piezoelectric cantilever sensor 12 is operateable at relative high frequencies in liquid media, gas media, and a vacuum. The piezoelectric cantilever sensor 12 thus provides extreme sensitivity to mass changes. The piezoelectric cantilever sensor 12 is especially suitable for analytes that are present at very low concentrations in complex media such as in body fluids, water, and food materials, for example.

The piezoelectric cantilever sensor 12 provides the ability to detect changes in mass accumulated thereon as small as 1 femtogram/Hz ($1\times10^{-18}$ grams/Hertz) or less when immersed in a liquid media. Thus, with respect to detecting changes in mass, the piezoelectric cantilever sensor 12 is approximately 1 billion times more sensitive than a 5 MHz quartz crystal micro-balance sensor, approximate one million times more sensitive than standard analytical instruments, and nearly a billion-fold more sensitive than conventional assay method known as enzyme-linked immunosorption assay (ELISA).

The piezoelectric cantilever sensor 12 permits detection of extremely small concentrations of analyte that bind to it. Utilizing the piezoelectric cantilever sensor, pathogens and proteins are detectable at concentrations as low as a few pathogens/mL and, for proteins of average size (60 kiloDaltons, kDa), at less than 10 fg/mL. Furthermore, any analyte that binds to an organic or inorganic functional group on the sensor is detectable. The piezoelectric cantilever sensor 12 is operable in media having relatively high flow rates. The piezoelectric cantilever sensor 12 is operable in media having flow rates of 0.5 to 10.0 mL/minute, which is approximately 1000 times the flow rate used successfully with known bending mode micro-cantilevers.

Various example applications of the piezoelectric cantilever include the detection of bioterrorism agents, such as *Bacillus anthracis*, the detection of food-borne pathogens, such as *E. coli*, the detection of pathogens in food and water, the detection of certain cell types in body fluids (e.g., circulating tumor cells), the detection of biomarkers in body fluids (e.g., proteins that mark specific pathophysiology-alpha-fetoprotein, beta-2-microglobulin, bladder tumor antigen, breast cancer marker CA-15-3, and other CAs (cancer antigens), calcitonin, carcinoembryonic antigen, and others), the detection of markers of explosives such as trinitrotoluene (TNT), the presence of dinitrotoluene (DNT), the detection of airborne and waterborne toxins, and the measurement of viscosity and density of fluids (liquids and gases). The piezoelectric cantilever sensor also can be used for the detection of biological entities at attogram levels, and for the detection of protein-protein interactions, both steady state and kinetic.

Pathogens, such as E-coli for example, are detectable utilizing the piezoelectric cantilever sensor 12. Detection of a model protein, lipoprotein, DNA, and/or RNA at a concentration less than 1.0 femtogram per mL ($10^{-15}$ grams) and pathogens at less than 1 pathogen/mL, respectively is achievable by measuring directly in liquid using the piezoelectric cantilever sensor immobilized with antibodies specific to the target analyte at a frequency of about 800 kHz to 1.8 MHz. The piezoelectric cantilever sensor 12 is capable of detecting a target analyte without false positives or negatives even when contaminating entities are present. The piezoelectric cantilever sensor 12 is particularly advantageous when utilized with a raw sample, and no preparation, concentrating step, and/or enrichment of any type. Detection of an analyte utilizing the piezoelectric cantilever sensor 12 can be conducted directly in raw samples under flow conditions, greater than 15 mL/minute, for example.

As described below, the sensitivity of the piezoelectric cantilever sensor 12 is due in part to the geometric design thereof. The relative lengths and widths of the piezoelectric layer 14 and the positioning of each layer with respect to other layers within the non-piezoelectric layer 16, of the piezoelectric cantilever sensor 12 determine the sensitivity, and also the shape of the peak of the frequency spectrum provided by the piezoelectric cantilever sensor 12. As described in more detail below, the piezoelectric cantilever sensor 12 comprises a piezoelectric layer 14 and a non-piezoelectric layer 16 coupled together.

The sensitivity of the piezoelectric cantilever sensor 12 is due in part to utilizing the piezoelectric layer 14 of the piezoelectric cantilever sensor 12 for both actuation and sensing of the electromechanical properties of the piezoelectric layer 14 of the piezoelectric cantilever sensor 12. At resonance, the oscillating cantilever concentrates stress toward an area of low bending modulus. This results in an amplified change in the resistive component of the piezoelectric layer 14 and a large shift in resonance frequency. Directing this stress to a portion of the piezoelectric layer 14 having a low bending modulus allows for exploitation of the associated shift in resonance frequency to detect extremely small changes in mass of the piezoelectric cantilever sensor 12. For example, if both the piezoelectric layer and the non-piezoelectric layer of a piezoelectric cantilever sensor are anchored at the same end (e.g., potted in epoxy), the sensor is less sensitive to changes in mass because the bending stress in the sensing piezoelectric layer proximal to the anchored end is lower compared to the case when only the piezoelectric layer is anchored. This is because the bending modulus of the two combined layers is higher than the case of anchoring the piezoelectric layer only. Bending modulus is the product of elastic modulus and moment of inertia about the neutral axis. And, moment of inertia is proportional to the cube power of thickness.

The piezoelectric portion 14 can comprise any appropriate material exhibiting piezoelectric properties, such as lead zirconate titanate, lead magnesium niobate-lead titanate solid solutions, strontium lead titanate, quartz silica, piezoelectric ceramic lead zirconate and titanate (PZT), piezoceramic-polymer fiber composites, or the like, for example. The non-piezoelectric portion 16 can comprise any appropriate material such as glass, ceramics, metals, polymers and composites of one or more of ceramics, and polymers, such as silicon dioxide, copper, stainless steel, titanium, or the like, for example.

The piezoelectric cantilever sensor can comprise portions having any appropriate combination of dimensions. Further, physical dimensions can be non-uniform. Thus, the piezoelectric layer and/or the non-piezoelectric layer can be tapered. For example, the length (e.g., $L_P$ in FIG. 9) of the piezoelectric portion (e.g., piezoelectric portion 14) can range from about 0.1 to about 10 mm. The length (e.g., $L_{NP}$ in FIG. 9) of the non-piezoelectric portion (e.g., non-piezoelectric portion 16) can range from about 0.1 to about 10 mm. The overlap region (e.g., overlap region 23) can range from about 0.1 to about 10 mm in length. The width (e.g., $W_P$ in FIG. 9) of the piezoelectric portion (e.g., piezoelectric portion 14), and the width (e.g., $W_{NP}$ in FIG. 9) of the non-piezoelectric portion (e.g., non-piezoelectric portion 16), can range from about 0.1 mm to about 4.0 mm. The width (e.g., $W_P$ in FIG. 9) of the piezoelectric portion can differ from the width (e.g., $W_{NP}$ in FIG. 9) of the non-piezoelectric portion as well. The thickness of the (e.g., $T_P$ in FIG. 9) of the piezoelectric portion (e.g., piezoelectric portion 14), and the thickness (e.g., $T_{NP}$ in FIG. 9) of the non-piezoelectric portion (e.g., non-piezoelectric portion 16), can range from about 10 micrometers ($10 \times 10^{-6}$ meters) to about 4.0 mm. The thickness (e.g., $T_P$ in FIG. 9) of the piezoelectric portion also can differ from the thickness (e.g., $T_{NP}$ in FIG. 9) of the non-piezoelectric portion.

Figure 10:
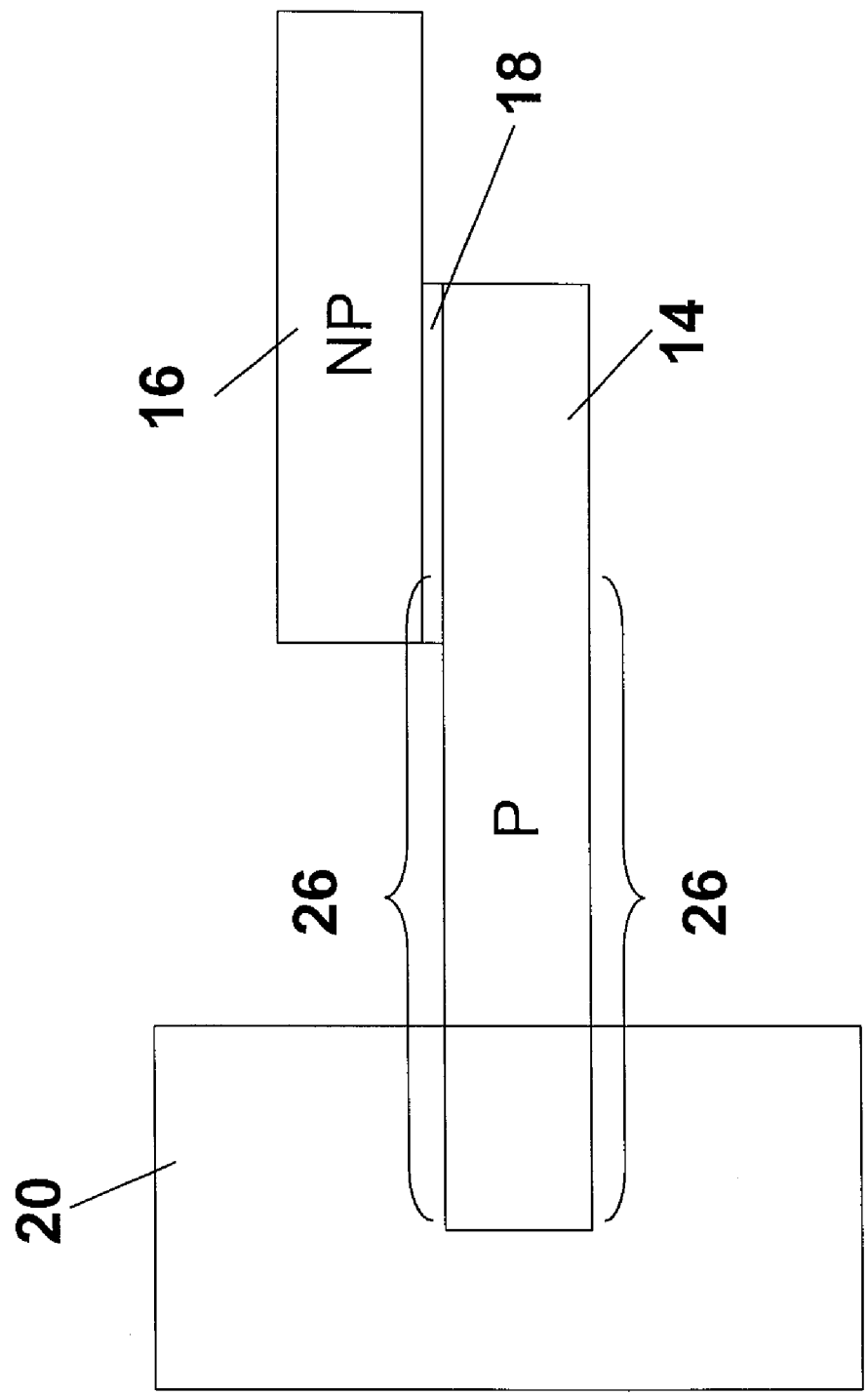
FIG. 10 is a cross-sectional view of an example piezoelectric cantilever sensor depicting electrode placement regions for electrodes operationally associated with the piezoelectric layer.
Figure 11:
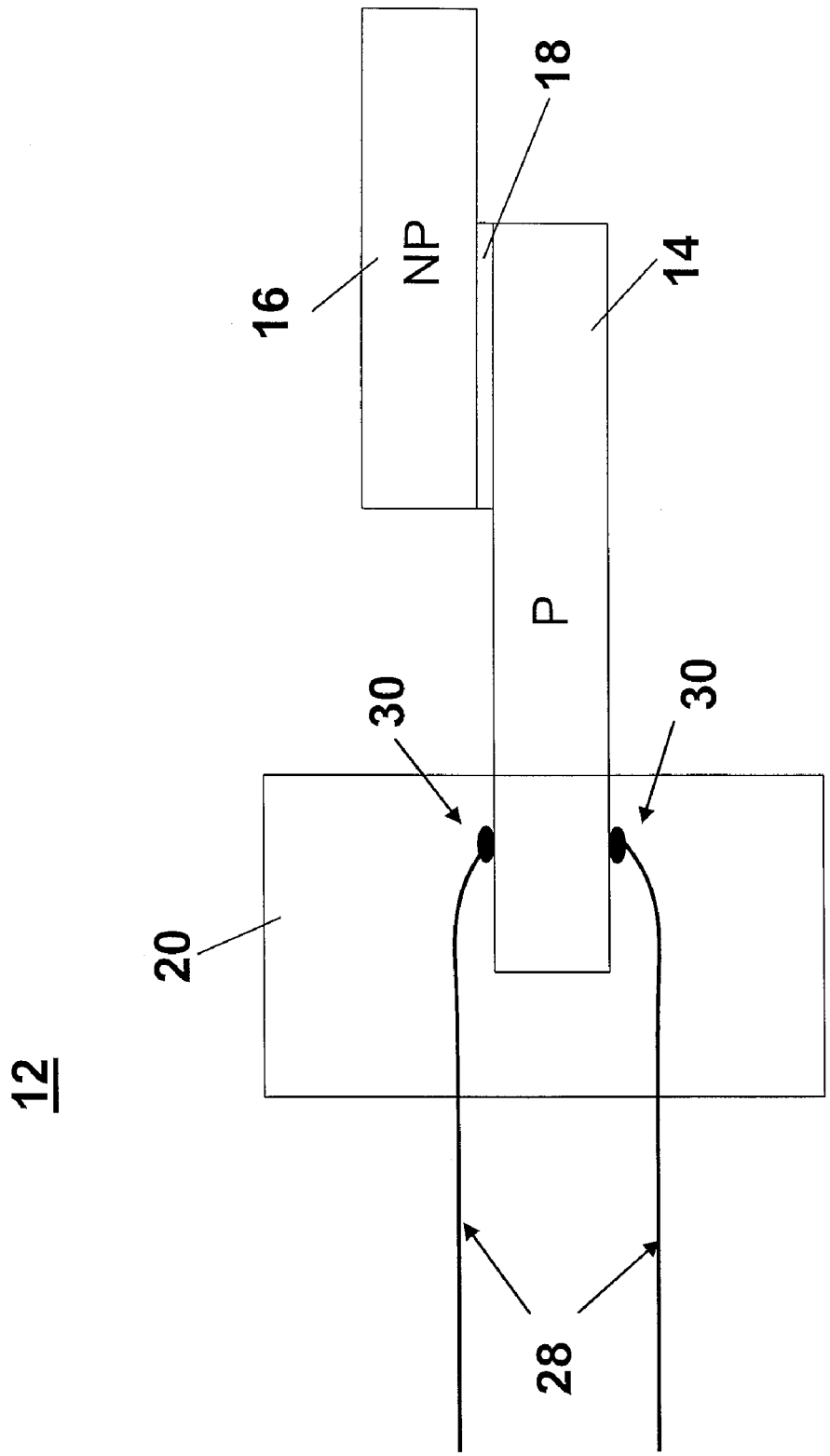
FIG. 11 is a cross-sectional view of an example piezoelectric cantilever sensor showing depicting example electrode placement within a base portion of the self-exciting, self-sensing piezoelectric cantilever sensor.
Figure 12:
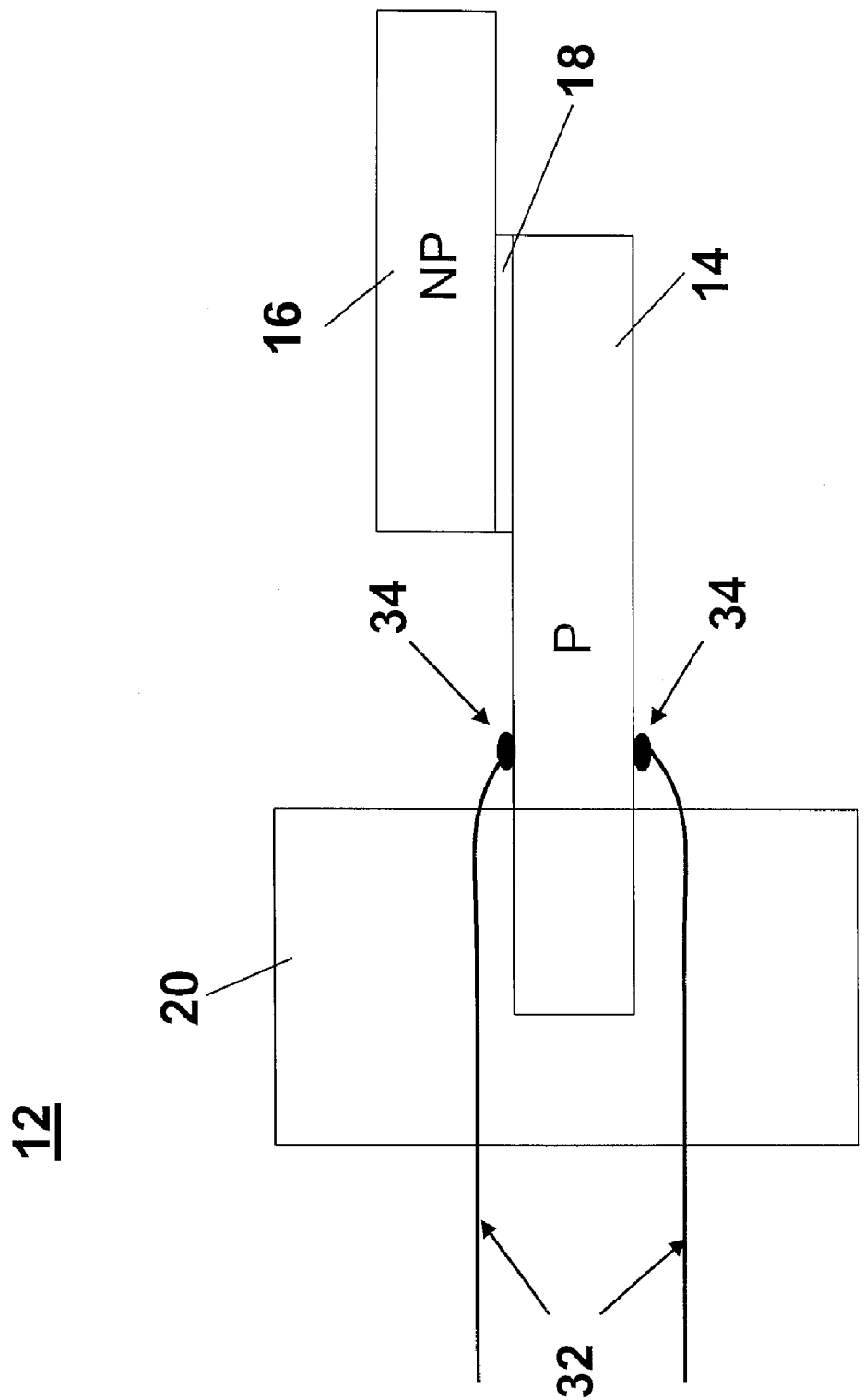
FIG. 12 is a cross-sectional view of an example piezoelectric cantilever sensor depicting example electrode placement not within a base portion of the self-exciting, self-sensing piezoelectric cantilever sensor.

FIG. 10 is a cross-sectional view of the piezoelectric cantilever sensor 12 depicting electrode placement regions 26 for electrodes operationally associated with the piezoelectric portion 14. Electrodes can be placed at any appropriate location on the piezoelectric portion of the piezoelectric cantilever sensor 12 as indicated by brackets 26. For example, as shown in FIG. 11, electrodes 28 can be coupled to the piezoelectric portion 14 within the base portion 20. Or, as depicted in FIG. 12, electrodes 32 can be coupled to the piezoelectric portion 14 at any location not within the base portion 20. Electrodes need not be placed symmetrically about the piezoelectric portion 14. In an example embodiment, one electrode can be coupled to the piezoelectric portion 14 within the base portion 20 and the other electrode can be coupled to the piezoelectric portion 14 not within the base portion 20. Electrodes, or any appropriate means (e.g., inductive means, wireless means), can be utilized to provide an electrical signal to and receive an electrical signal from the piezoelectric portion 14. In an example embodiment, electrodes can be coupled to the piezoelectric portion 14 via a bonding pad or the like (depicted as elements 30 in FIG. 11 and elements 34 in FIG. 12). Example bonding pads can comprise any appropriate material (e.g., gold, silicon oxide) capable of immobilization of a receptor material and/or an absorbent material appropriate for use in chemical sensing or for bio-sensing.

Electrodes can be placed at any appropriate location on the piezoelectric cantilever sensor 12. In an example embodiment, electrodes are operatively located near a location of concentrated stress in the piezoelectric layer 14. As described above, the sensitivity of the piezoelectric cantilever sensor is due in part to advantageously directing (concentrating) the stress in the piezoelectric layer 14 and placing electrodes proximate thereto. The configurations of the piezoelectric cantilever sensor described herein (and variants thereof) tend to concentrate oscillation associated stress in the piezoelectric layer 14. At resonance, in some of the configurations of the piezoelectric cantilever sensor 12, the oscillating cantilever concentrates stress in the piezoelectric layer 14 toward the base portion 20. This results in an amplified change in the resistive component of the piezoelectric layer 14 and a large shift in phase angle at resonance frequency at the locations of high stress. Directing this stress to a portion of the piezoelectric layer 14 having a low bending modulus allows for exploitation of the associated shift in resonance frequency to detect extremely small changes in mass of the piezoelectric cantilever sensor 12. Thus, in example configurations of the piezoelectric cantilever sensor 12, the thickness of the piezoelectric layer 14 located near the base portion 20 is thinner than portions of the piezoelectric layer 14 further away from the base portion 20. This tends to concentrate stress toward the thinner portion of the piezoelectric layer 14. In example configurations, electrodes are located at or near the locations of the oscillation associated concentrated stress near the base portion of the piezoelectric cantilever sensor. In other example configurations of the piezoelectric cantilever sensor electrodes are positioned proximate the location of concentrated stress in the piezoelectric layer regardless of the proximity of the concentrated stress to a base portion of the piezoelectric cantilever sensor.

Figure 13:
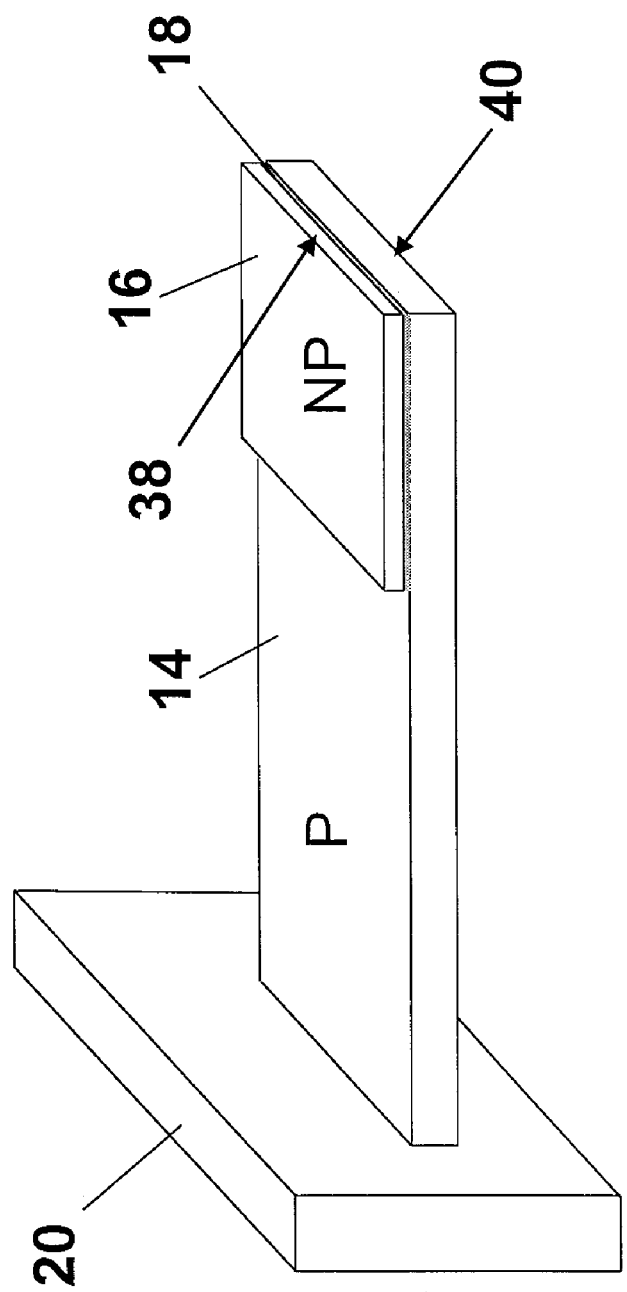
FIG. 13 is an illustration of an example configuration of a piezoelectric cantilever sensor wherein the distal end of the piezoelectric layer is flush with the distal end of the non-piezoelectric layer.
Figure 14:
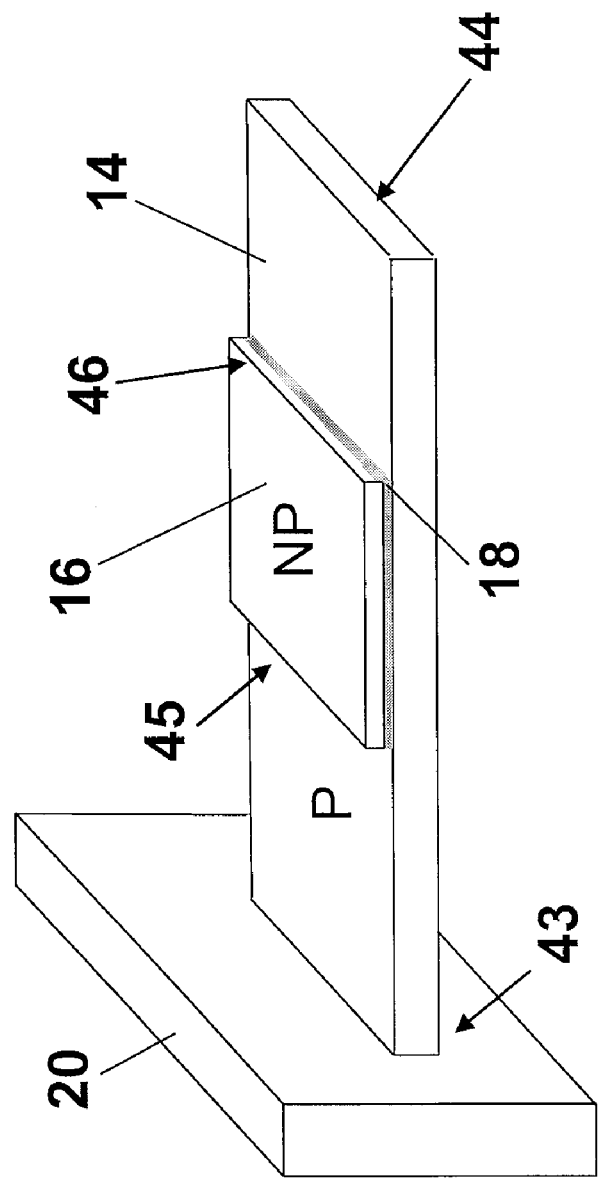
FIG. 14 is an illustration of an example configuration of a piezoelectric cantilever sensor wherein the distal end of the piezoelectric layer extends beyond the distal end of the non-piezoelectric layer and the proximate end of the piezoelectric layer extends beyond the proximate end of the non-piezoelectric layer.

The piezoelectric cantilever sensor can be configured in accordance with a plurality of configurations, some of which are depicted in FIG. 13 and FIG. 14. It is to be understood however, that the configurations depicted herein do not represent all possible configurations, but rather a representative sample of configurations of the piezoelectric cantilever sensor. FIG. 13 is an illustration of an example configuration 36 of an unanchored piezoelectric cantilever sensor wherein the distal end 40 of the piezoelectric portion 14 is flush with the distal end 38 of the non-piezoelectric portion 16. The piezoelectric cantilever sensor 36 is termed "unanchored" because the non-piezoelectric portion 16 is not attached to the base portion 20. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to a base portion 20.

FIG. 14 is an illustration of an example configuration 42 of an unanchored piezoelectric cantilever sensor wherein the distal end 44 of the piezoelectric portion 14 extends beyond the distal end 46 of the non-piezoelectric portion 16 and the proximate end 43 of the piezoelectric portion 14 extends beyond the proximate end 45 of the non-piezoelectric portion 16. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to the base portion 20.

Figure 15:
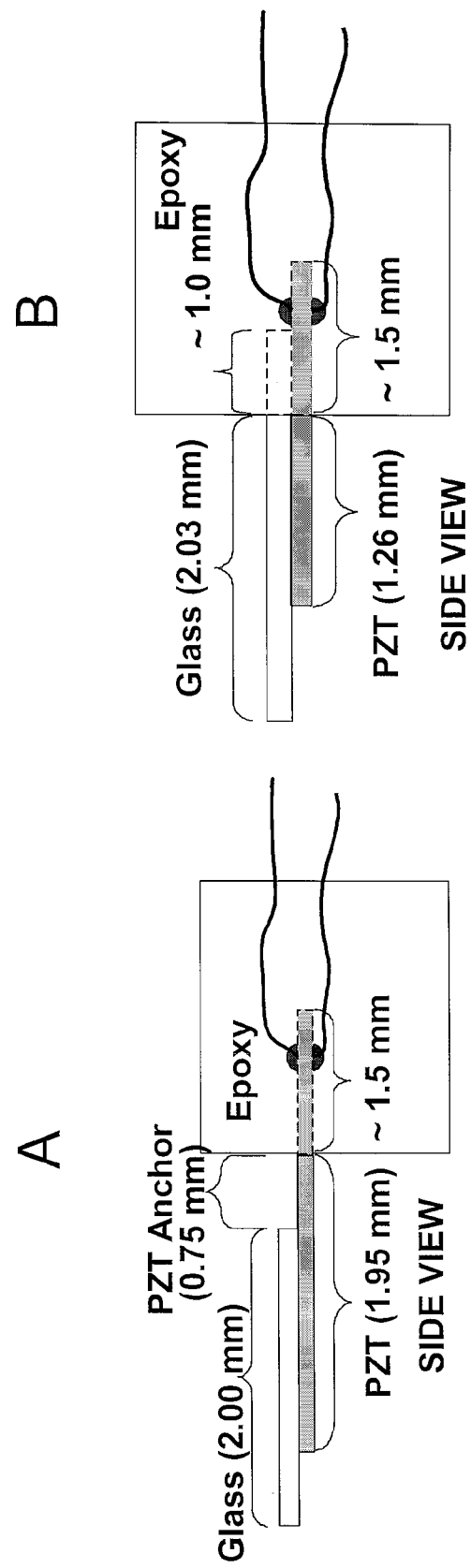
FIG. 15 is an illustration of a cross sectional view of two example piezoelectric cantilever sensor configurations A and B, wherein, in configuration A, the non-piezoelectric portion is not in contact with the base, and in configuration B, the non-piezoelectric portion is in contact with the base.

FIG. 15 is an illustration of cross sectional view of two example piezoelectric cantilever sensor configurations A and B. As depicted in configuration A, the non-piezoelectric portion is not in contact with the base. As depicted in configure B, the non-piezoelectric portion is in contact with the base.

Figure 16:
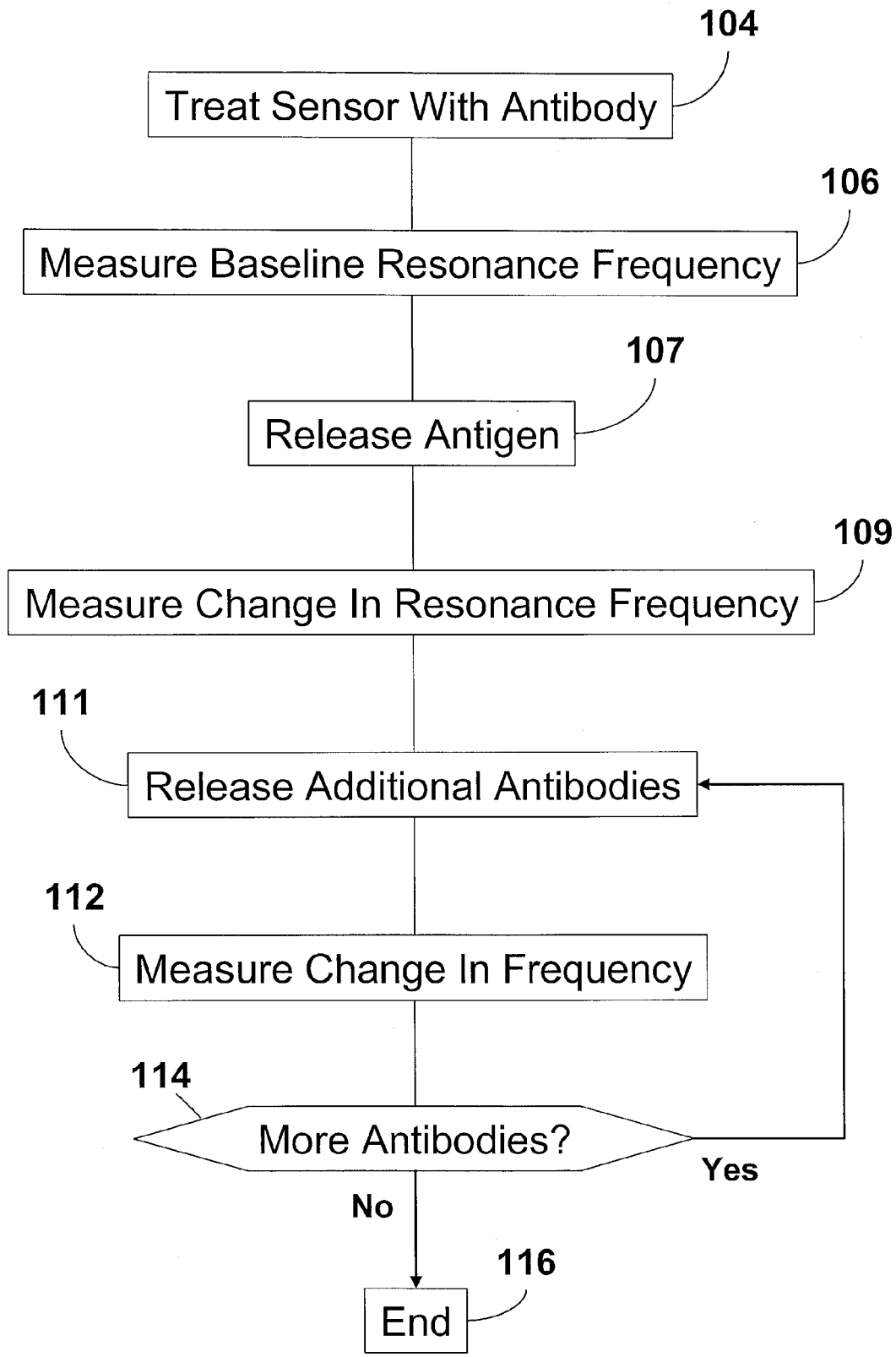
FIG. 16 is a flow diagram of an example process for enhanced sensitivity of a cantilever sensor via additional antibody binding.

FIG. 16 is a flow diagram of an example process for using a self-excited piezoelectric cantilever sensor with additional antibody binding. At step 104, the non-piezoelectric portion of a piezoelectric cantilever sensor is treated with an antibody corresponding to a selected antigen. Utilization of a piezoelectric cantilever sensor permits detection of extremely small concentrations of antigens that bind to the non-piezoelectric portion thereof. In an example application, described further below, the self-excited piezoelectric cantilever is utilized to detect amounts of $E.\ coli$ O157:H7 in a liquid medium, by placing goat-polyclonal a-EC, on the sensor surface. The $E.\ coli$ O157:H7 binds to the goat-polyclonal a-EC, adding mass to the sensor surface. This added mass changes the resonance frequency to the self-excited piezoelectric cantilever sensor, allowing for the change in mass to be measured by the change in frequency.

At step 106, a baseline resonance frequency is established for the self-excited piezoelectric cantilever sensor in the selected medium. The sensor is operable to detect antigens in fluid media (liquid and/or gas) in a chamber. In an example embodiment described below, the sensor is placed in a liquid medium in a chamber and the baseline frequency of the sensor is measured.

At step 107, the gas or liquid medium to be tested for the desired antigen is released into the chamber containing the sensor at a selected flow rate. If the desired antigen (also referred to as a target analyte) is present in the medium, the desired antigen attaches to the antibody that was immobilized on the piezoelectric cantilever sensor. In the example embodiment described below, an agitated solution of $H_2O$, ground beef and $E.\ coli$ is released into the chamber at a flow rate of 0.5-1.0 mL/min.

At step 109, the resonance frequency of the sensor is measured as the antigen attaches to the antibodies on the sensor's surface. As the antigen attaches to the antibodies, the mass of the sensor begins to increase, resulting in a change of the resonance frequency. The resonance frequency is continued to be measured until it stabilizes.

At step 111, a solution containing additional antibodies is released into the chamber. As described above, some antigen may have attached to the antibodies on the sensor surface, resulting in a change of mass on the sensor. The additional antibodies may attach to the antigen that has attached to the antibodies already on the sensor. These additional antibodies may result in a further increase of the mass of the sensor resulting in a further change of sensor resonate frequency.

At step 112, the resonance frequency of the sensor is measured to determine if there has been a further increase in mass. Any further increase in mass is further evidence that the target antigen has attached to the antibodies on the sensor. In addition, because the initial concentration of antigen in the solution may have been low, resulting in a very small change of mass to the sensor, adding additional antibodies can help verify that the desired antigen was present in the solution.

Binding additional antibodies to previously bound antibodies can further increase the effective mass of the sensor. If additional antibodies are to be utilized (step 114), additional antibodies are released (step 111) and the resonance frequency is measured (step 112). This process can be repeated as many times as desired. If no additional antibodies are to be utilized (step 114), the process ends at step 116.

Application of Additional Specific Bindings to Detect of $E.\ Coli$

The foregoing process using additional specific bindings and a piezoelectric millimeter sized cantilever (PEMC) sensor were utilized to detect t $Escherichia\ coli$ O157:H7. Goat polyclonal anti-$Escherichia\ coli$ O157:H7 antibody was used. The antibody is highly specific for type O157:H7. Antibody cross-reactivity to other strains of $E.\ coli$ is minimized through extensive adsorption using non-O157:H7 $E.\ coli$. Radiation killed $E.\ coli$ samples were prepared in a phosphate buffered saline (PBS) solution (10 mM, pH 7.4) by serial dilution to concentrations of 100, 1,000, 10,000, and 100,000 cells/mL. Commercially purchased ground beef (2.5 g) was weighed into polypropylene tubes containing 10 mL of PBS. The content was mixed for 2 minutes using a bench top vortex mixer. A one mL aliquot of $E.\ coli$ sample was added to each beef containing tube to final concentrations of 10, 100, 1,000, and 10,000 cells/mL. The $E.\ coli$ and ground beef suspensions were mixed by manually inverting the polypropylene tubes 10 times over five minutes. Prior to removing the test sample, the mixed solution was allowed to sit undisturbed for 10 minutes. A 1 mL of sample solution was removed from the beef containing tubes and injected into a flow circuit. The sample flow circuit has a 3 mL hold up volume, therefore, a one-mL sample containing concentrations of 10, 100, 1,000, and 10,000 cells/mL was diluted to an effective concentration of 3, 25, 250, and 2,500 cells/mL, respectively. The concentration values reported herein are in terms of sample concentration.

Figure 17:
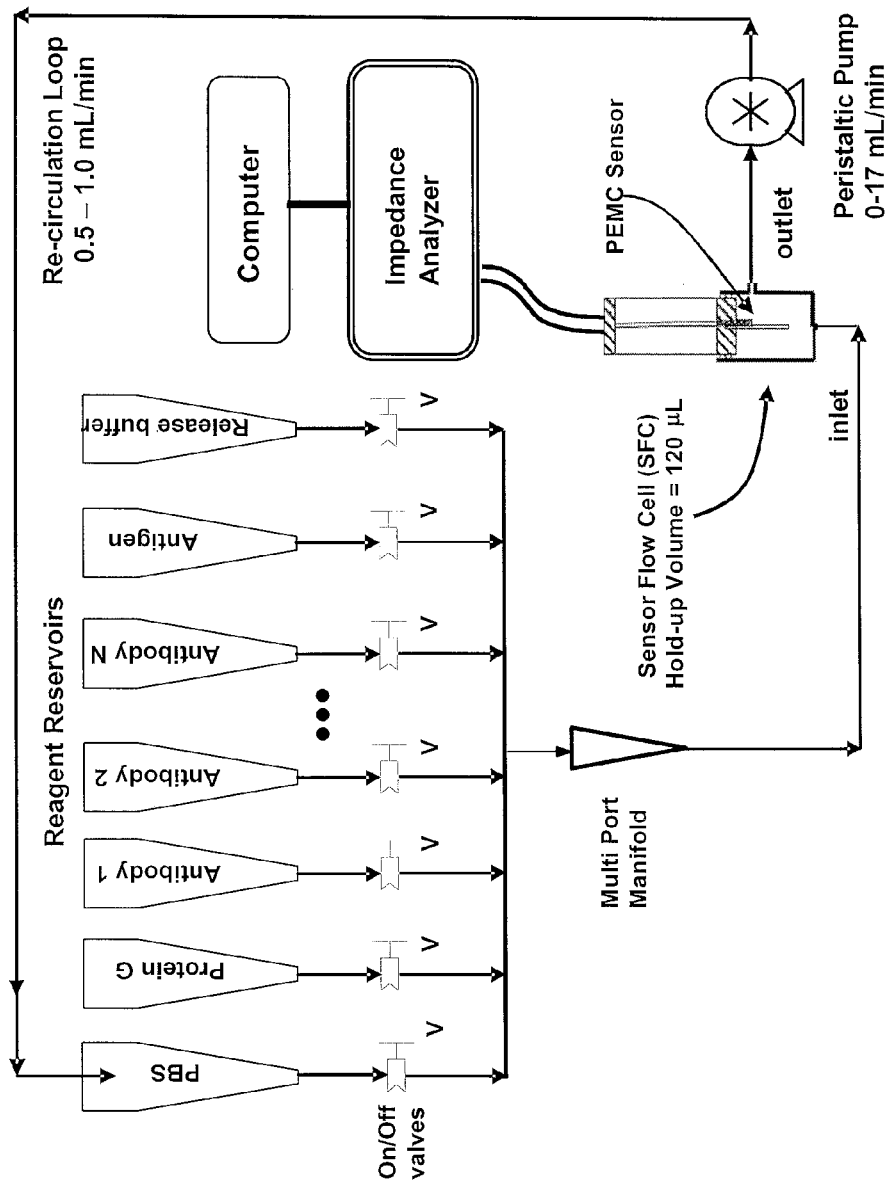
FIG. 17 is a schematic of experimental apparatus utilizing a piezoelectric cantilever sensor.

A schematic of the experimental setup is given in FIG. 17. The experimental setup included five fluid reservoirs, a peristaltic pump, and a sensor flow cell (SFC). Although a system having five reservoirs was used, FIG. 17 depicts multiple reservoirs for multiple antibodies, antibody 1, antibody 2, through antibody N, wherein N is an appropriate integer. A reagent reservoir manifold containing five chambers was connected via a five port manifold to the inlet of the SFC. A peristaltic pump was connected to the outlet of the SFC and was used to maintain the flow rate between 0.5 and 1.0 ml/min. The PEMC sensor was inserted into the SFC and the electrodes were connected to an impedance analyzer interfaced with a computer to obtain impedance and phase angle measurements in the frequency range of 10 kHz and 1.8 MHz. The experimental apparatus allowed for a single pass through the SFC as well as recirculation of reagent during antibody immobilization. The sensor flow cell (SFC) had a well diameter of 7.0 mm with a hold-up volume of 120 μL after the sensor was installed. The inlet and outlets were located at the bottom and on the side of the cell, respectively, approximately 4 mm apart. Each of the five fluid reservoirs were allocated for PBS (10 mM, pH 7.4), Protein G (100 μg/mL), antibody (10 μg/mL), test sample, and release solution (PBS/Hal, pH=2.2). The liquid reservoirs were connected to the inlet of the SFC via a five-entrance port manifold with a single outlet. The outlet of the flow cell was connected to a peristaltic pump, which controlled the flow of the desired fluid into and out of the SFC.

The functionalized sensor was installed vertically into the SFC filled with PBS. The cantilever electrodes were connected to an impedance analyzer interfaced to a PC comprising an application for recording impedance and phase angle measurements in the frequency range of 40 kHz to 1.5 MHz. Resonant frequency values were recorded every 30 seconds and the mean value was calculated over a 2.5 minute period. The SFC was maintained at 30±0.1° C. by circulating (17 mL/min) constant temperature water 38±0.1° C. through a jacket surrounding the SFC. Valves located at the bottom of each of the fluid reservoirs enabled the selection of the fluid for flow into the SFC or for circulation. Switching the outlet line from the peristaltic pump into the desired fluid reservoir enabled total recirculation, when needed.

The sensors used in the experiments were used directly after gold coating the glass surface of the sensor. The sensor was installed in the sample flow cell and stabilized with 10 mM PBS for 10 minutes. The gold sensor surface was exposed to Protein G followed by PBS, and finally antibody solution in succession at 0.5 mL/min in a recirculation mode. After each detection experiment, the sensor surface was cleaned and re-used. After three such re-uses, it was recoated.

The detection experiments were carried at flow rates of 0.5-1.0 mL/min. PBS solution was re-circulated through the SFC to ensure the tubing and SFC was flushed prior to a detection experiment. The measured resonant frequency of the cantilever sensor was monitored until it stabilized before antibody immobilization and subsequent antigen detection. After stabilizing the sensor in PBS, 1 mL of 100 μg/mL Protein G was flowed past the surface for 75 minutes to attach the protein to the sensor surface. Protein G was introduced to orient the antibody on the sensor surface. Once the Protein G attachment was complete, a PBS flush was performed and one mL of 10 μg/mL antibody was flowed past the surface for 90 minutes followed by an additional PBS flush. Typical frequency response of the PEMC sensor to Protein G and antibody was 1.3±0.4 (n=20) and 0.9±0.4 (n=15) kHz, respectively, for the ten sensors that were used. For a given sensor, the variance for Protein G and antibody immobilization was far less, typically 1.2±0.1 and 0.8±0.07 kHz, respectively. Prior to detection, each sample tubes containing *E. coli* and ground beef were agitated to ensure proper mixing, and then allowed to sit undisturbed for 10 minutes prior to sampling the supernatant. During this time, the large chunks of beef and particles settled to the bottom of the tube. A one-mL sample was removed from the sample supernatant and was added to the sample reservoir. Detection was initiated by flowing the sample past the sensor surface at 0.5-1.0 mL/min in recirculation mode until steady state was reached. Steady state was assumed to have been reached if the sensor resonance frequency was within ±30 Hz for a minimum of 10 minutes. Since the total volume in the flow circuit was approximately 3 mL, a ten minute time course would allow 3-4 fluid exchanges, which is sufficient to ensure the previous solution has been cleared from the circuit. After this, the flow circuit was rinsed with PBS followed by the release buffer to release the bound antigen. Finally, a PBS flush was carried out until the resonant frequency value reached steady state to remove weakly attached and suspended particles. To confirm that the sensor response was due to antigen binding, both positive and negative control samples were carried out at the same temperature and flow rate. The positive control was response of PEMC sensor that was not prepared with the antibody and exposed to 100,000 cells/mL *E. coli*. Negative control was the response of antibody-immobilized PEMC sensor to a one-mL sample of ground beef in PBS at 1.0 mL/min.

Figure 18:
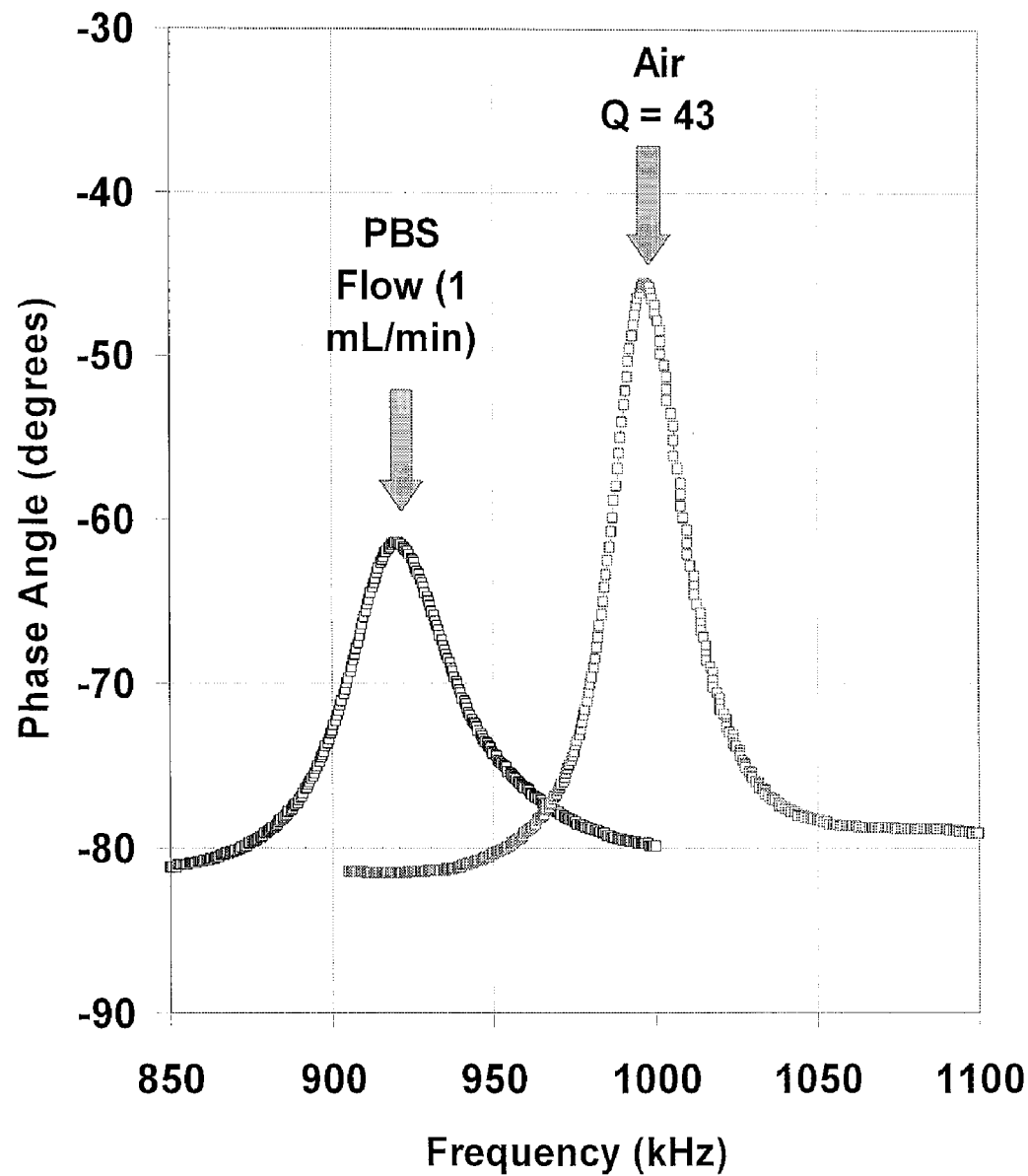
FIG. 18 is an illustration of the resonance spectrum of a piezoelectric cantilever sensor.

Approximately 10 cantilever sensors were fabricated and used in the referenced detection experiments. The resonance mode located at 997 kHz was used in all of the detection experiments and is shown in FIG. 18. The spectra, a plot of phase angle versus excitation frequency, shows one resonant peak in air at 997.0±0.05 kHz. When the sensor was submerged in PBS at 1.0 mL/min the resonance frequency decreased to 920.0±0.05 kHz. Also the peak height decreases in liquid by ~30%, due to damping. Peak quality (Q-factor) decreased from 43 to 29 in going from air to liquid flow conditions. The resonance frequency decreased from 997 to 920 kHz in PBS under 1 mL/min flow conditions and had a Q of 43 and 29, respectively. The sensors used in the experimental plan were chosen from the subset of 10 that exhibited similar characteristics.

Ground beef samples inoculated with *E. coli* O157:H7 were prepared as described above. Plots A and B show the sensor response to *E. coli* attachment at 0.5 mL/min for various beef samples in a ground beef wash. Ground beef wash was prepared by adding 2.5 g of ground beef to 10 mL of 10 mM PBS and vigorously mixed. The supernatant was removed without centrifuging and served as the ground beef wash. The three curve groupings in plot A represent 100, 1,000 and 10,000 cells/mL. Rate of binding depends on concentration. The control is an antibody-immobilized sensor in PBS (pH 7.4) flowing at 1.0 mL/min. Response is 2±7 Hz. In plot B, the control, an antibody-immobilized cantilever in PBS (pH 7.4) at 1.0 mL/min, provides a response of 4±9 Hz. A positive and negative control yields an essentially zero response of 36±6 and 27±2 Hz, respectively. The positive control is the response of PEMC sensor to EC containing sample, but the sensor is not immobilized with the antibody. Negative control is the response of antibody-immobilized PEMC sensor to ground beef in PBS at 1.0 mL/min, but the sample is not spiked with EC. In all cases, the frequency response showed a rapid decrease during the first 10 minutes followed by a slower change that reached a constant value within 40 minutes. Experiments in plots A and B were carried out at 10, 100, 1,000, and 10,000 cells/mL and resulted in resonant frequency decreases of 138±9 (n=2), 735±23 (n=2), 2,603±51 (n=1), and 7,184±606 (n=2) Hz, respectively. The sensitivity of the PEMC sensors in the range of 0.3 to 2 fg/Hz. The magnitude of frequency response for the lowest concentration of E. coli (10 cells/mL) is well within the sensors proven limit of detection, For the highest cell concentration (10,000 cells/mL), the rate of decrease was more rapid compared to the lowest concentration (10 cells/mL) sample. This is an expected response since the binding rate is proportional to antigen concentration. Positive and negative controls yielded an essentially zero response of 36±6 and 27±2 Hz, respectively. Additionally, a reference sample containing PBS only was analyzed and yielded a zero response (2±7 Hz).

During a typical detection experiment, only a small fraction of the total cells in the liquid bind to the sensor because of local fluid dynamics. Assuming that the sensor oscillation amplitude is on the order of a few nanometers and an average flow rate of 0.5 mL/min, the average residence time in the sample flow cell is about 12 seconds. Given that a mean diffusion rate of E. coli cell can be approximated as $8.2 \times 10^{-7}$ cm$^2$/s, the diffusional transport is small, and the sensor senses only a small volume. Therefore, the frequency change observed is due to detection of a small percentage of total cells in solution. Further optimization of the current experimental design is being explored to increase the probability of the target pathogen contacting the sensor surface.

Figure 19:
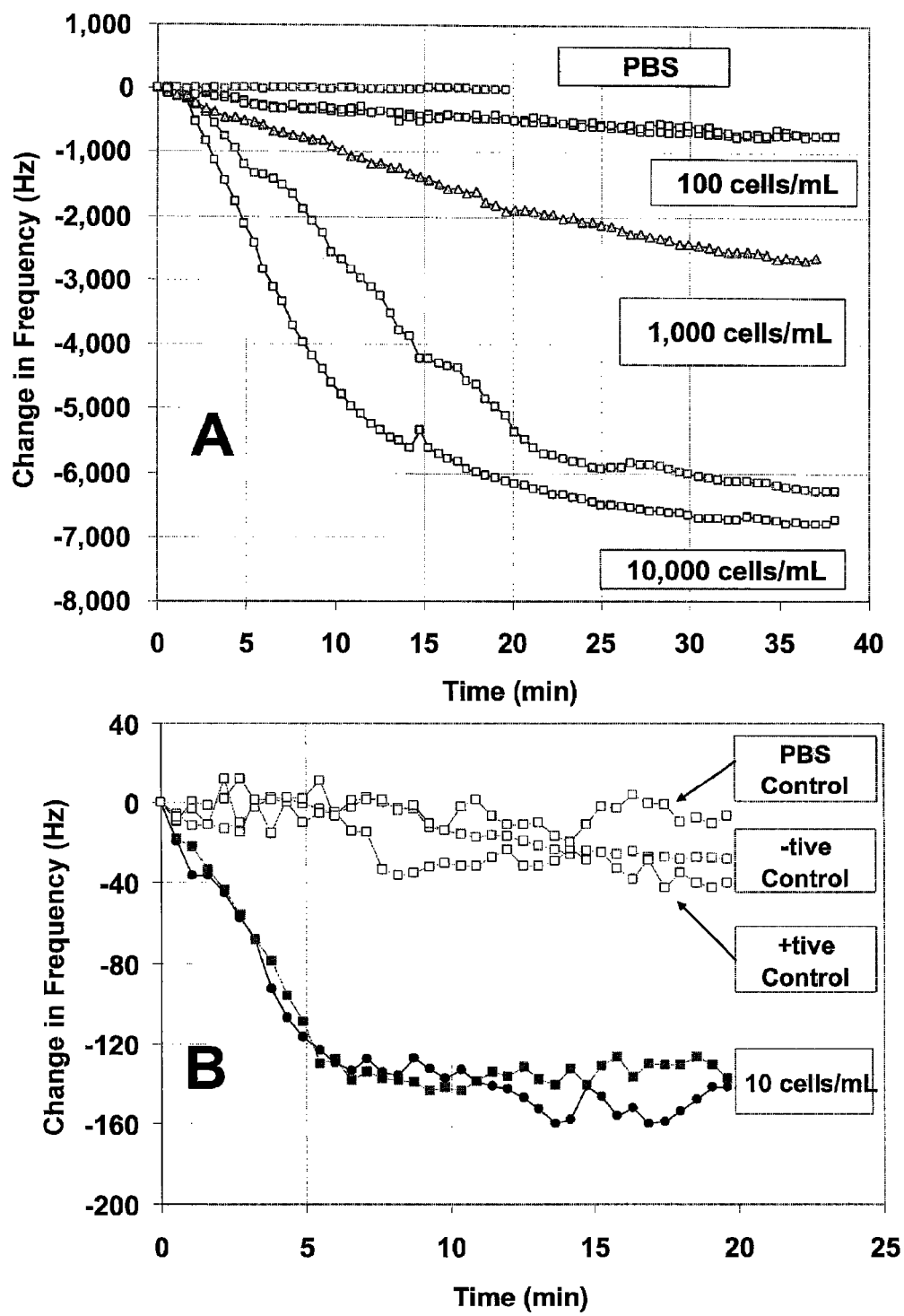
FIG. 19, depicting plots A and B, is an illustration of resonance frequency decrease upon binding of *E. coli* O157:H7 to the antibody-immobilized sensor surface at various concentrations in a ground beef wash and is an illustration of resonance frequency response upon binding of a sample containing 10 cells/mL of *E. coli*.
Figure 20:
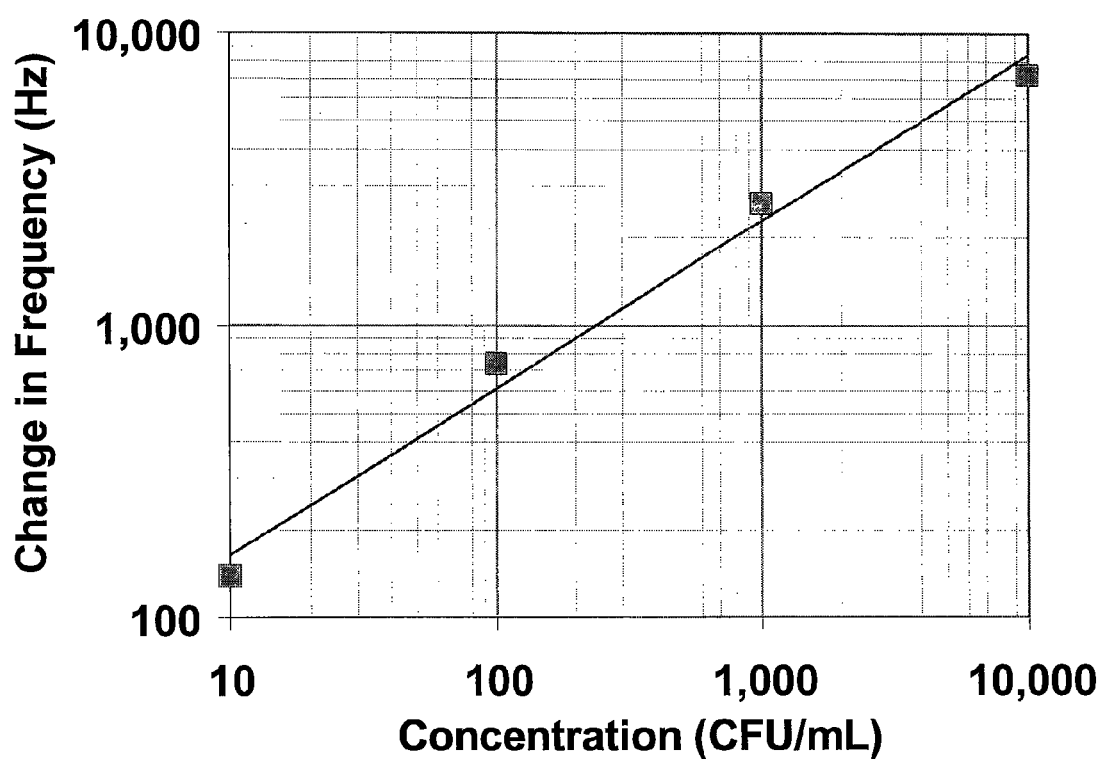
FIG. 20 is an illustration of resonance frequency change as a function of *E. coli* concentration.

Plotting the sensor response data from FIG. 19 versus the log of E. coli concentration in the beef samples gives rise to curves showing resonant frequency change increases in a nearly log-linear fashion with concentration in the 100-10,000 cells/mL range (data not shown). Thus, a calibration relationship exists for estimating concentration from sensor response and can be stated as:

$$\log(C_{b0}) = \frac{(-\Delta f) + A}{B} \quad (1)$$

where A is the y-intercept and B is the slope of the resulting line. The term $(-\Delta f)$ is the steady state resonance frequency change and $C_{b0}$ is the concentration of E. coli (EC) in the sample. The parameters A and B depend on cantilever dimensions, antibody binding constant, and antibody surface concentration. Fitting the data in plot A of FIG. 19 to Equation (1) yields a straight line gave a correlation coefficient of 0.95, with A=6166.2 and B=1400.4. Equation (1) does not hold at very low concentrations of 10 cell/mL, as the correlated value deviates from experimental data. Examining the frequency response over the entire concentration range investigated (10-10,000 cells/mL) gives rise to the following logarithmic relationship:

$$\log(C_{b0}) = \left(\frac{\log(-\Delta f)}{B}\right)^A \quad (2)$$

where A and B are correlation constants. Fitting the data in FIG. 19 to Equation (2) gives a correlation coefficient of 0.99, with A=1.75 and B=44.14 (FIG. 20). The graph shown in FIG. 20 is a log plot of the sensor response data from FIG. 19 plots A and B versus the log of E. coli concentration in the beef samples. Fitting data obtained for B. anthracis with Equation (2) gives a correlation coefficient of 0.93, with A=2.88 and B=19.38. Since higher order modes are more sensitive, the resonant peak used for detecting EC would have given rise to a higher frequency change for the corresponding sample concentrations.

One way to obtain confirmation that the observed resonance frequency decrease is indeed due to EC attachment on the sensor surface, is to determine if antibody will attach to already detected EC on the surface. Since the antibody used in this investigation was a goat polyclonal, the antibody binding sites on EC will still be accessible even though EC is surface-immobilized. For the case of a 100 cells/mL experiment, subsequent to detection and PBS flush, one mL of 10 μg/mL of antibody was pumped into the flow cell in recirculation mode for 30 minutes. The 100 cells/mL sample resulted in a frequency change of 1267±17 Hz (FIG. 20) and the PBS flush created a very small further change. The antibody caused a further resonant frequency decrease of 288±11 Hz. The decrease due to binding of antibody to the sensor-bound cells confirms that the frequency decrease observed during detection was due to E. coli O157:H7 binding to the sensor. The response to antibody was almost one-fifth of that due to the cells.

Figure 21:
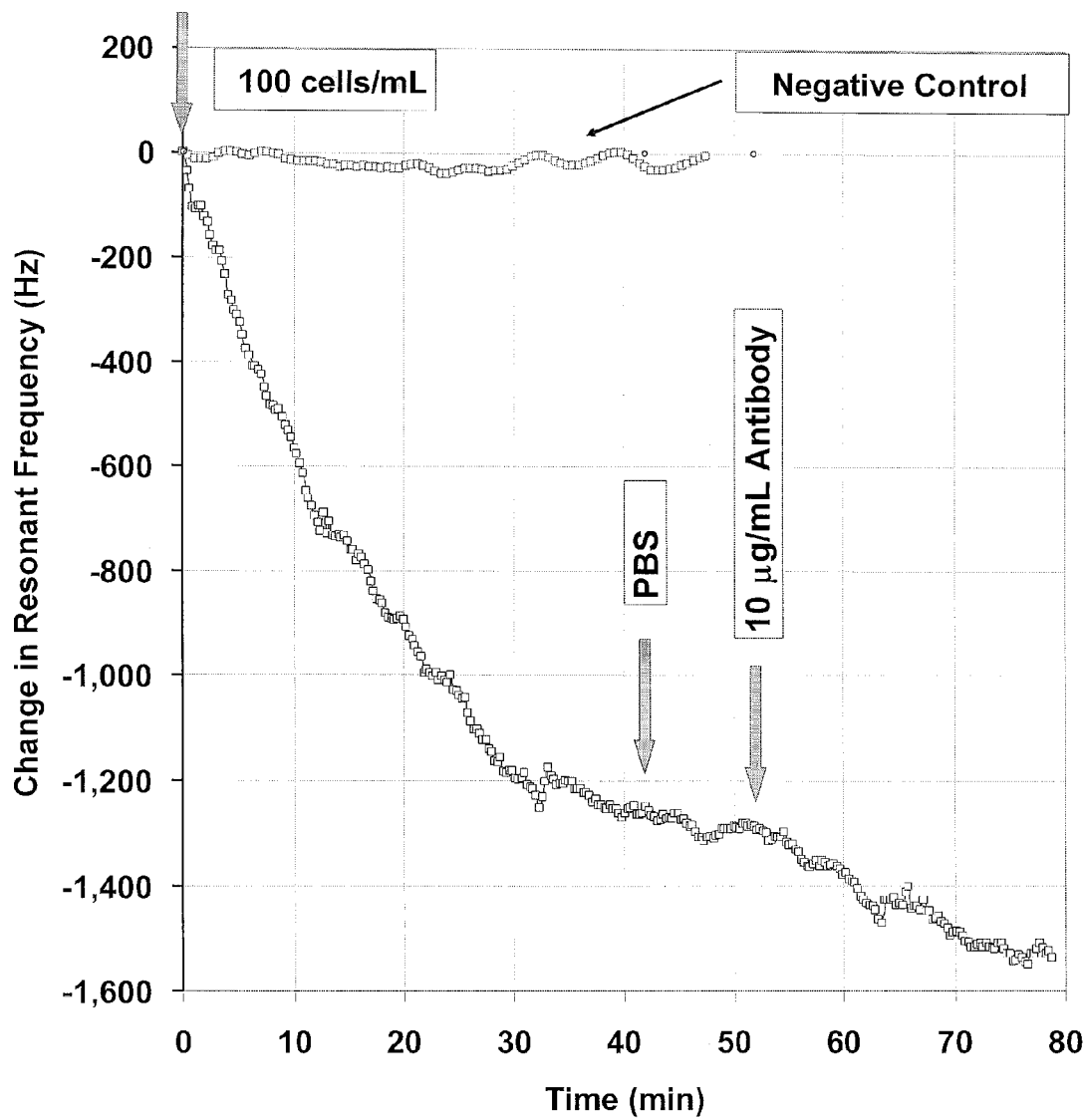
FIG. 21 is an illustration of a "Sandwich" response.

FIG. 21 is an illustration of a "Sandwich" response. First the PEMC sensor was exposed to 100 cells/mL of ground beef wash for 43 minutes, followed by PBS (11 min) and then goat polyclonal antibody (10 μg/mL) to EC. The initial attachment of cells caused a resonance frequency decrease of 1,267±17 Hz, and the second antibody flow caused a decrease of 288±11 Hz.

Figure 22:
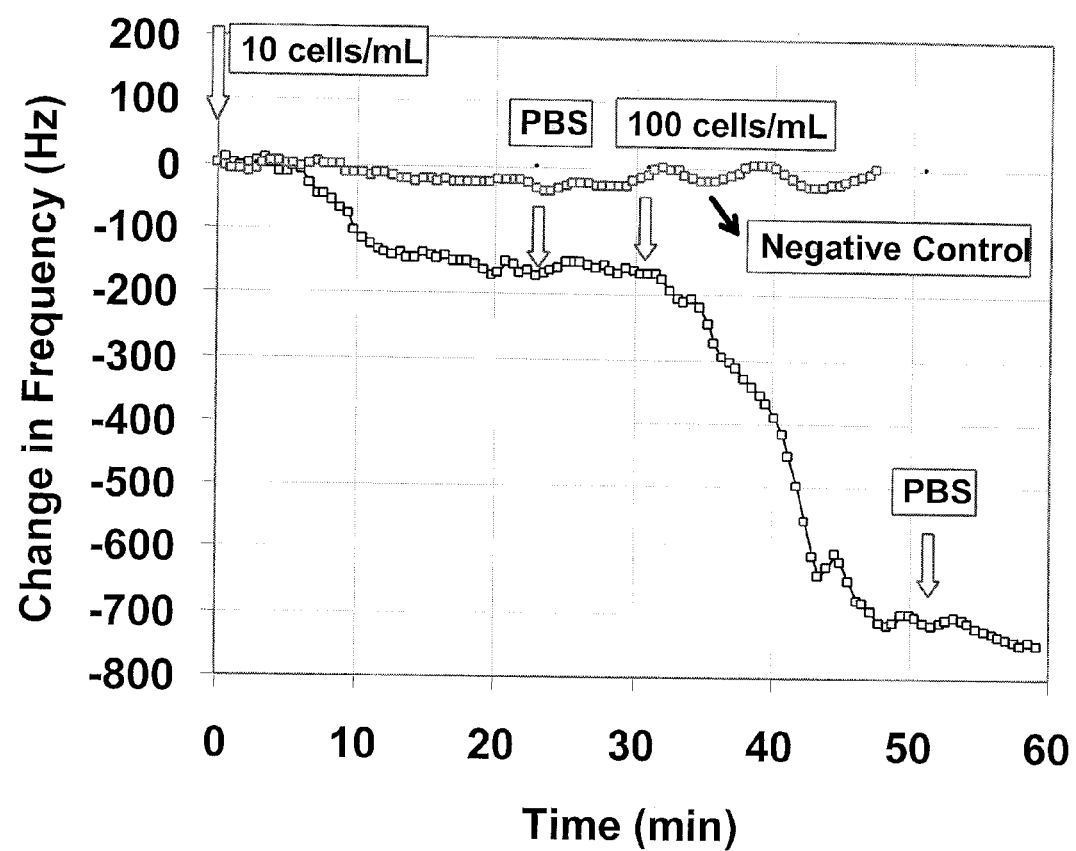
FIG. 22 is an illustration of sequential exposure of 10 and 100 cells/mL sample prepared in ground beef plus PBS buffer to an antibody-immobilized sensor.

Sensor response to increasing concentrations of E. coli O157:H7 in beef samples was also analyzed. A ground beef sample containing 10 cells/mL was flowed past the sensor surface at 1.0 mL/min followed by a PBS flush and a second sample containing 100 cells/mL. The results shown in FIG. 22 indicate a sensor response of 191±32 and 683±46 Hz, respectively, for the two concentrations. Following the sample, PBS flush resulted in a slight frequency decrease (~35 Hz) which may have been due to the density difference between the buffer and the beef sample. The sensor response to 10 cells/mL and 100 cells/mL is 191±32 and 683±46 Hz, respectively. For comparison, the PBS Control (2±7 Hz) is included in the graph.

Figure 23:
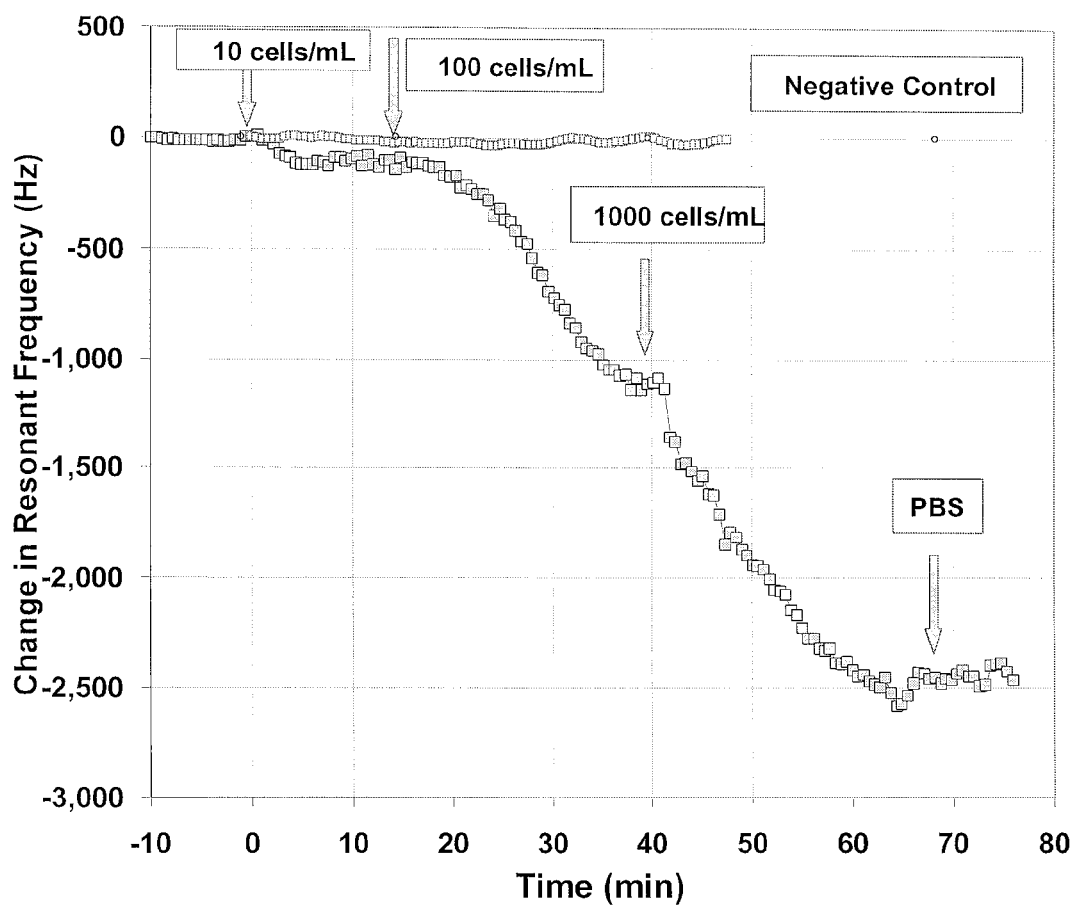
FIG. 23 is an illustration of the attachment of *E. coli*, completed by sequentially flowing 10, 100, and 1,000 cells/mL samples past the sensor surface.

Another sequential attachment was conducted by serially flowing 10, 100, and 1,000 cells/mL samples of ground beef and is shown in FIG. 23. FIG. 23 is an illustration of the attachment of E. coli, completed by sequentially flowing 10, 100, and 1,000 cells/mL samples past the sensor surface. Samples are prepared in 2.5 g ground beef in 10 mL PBS buffer. The frequency change resulting from the sequential addition was 122±5, 991±12, and 1,343±34 Hz, for a total frequency change of 2,456 Hz. Following EC attachment, PBS flush resulted in a 80 Hz increase.

The post-detection PBS flush resulted in a resonant frequency change ranging between −40 and +80 Hz. The change resulting from the PBS flush is small in comparison with the change resulting from EC detection. The resultant frequency change during the PBS flush was small in comparison with the frequency change due to lowest concentration of EC in the samples (10 cells/mL). At the lowest concentration (10 cells/mL) the response level ranged from 122 to 191 Hz depending on the sensor and antibody-immobilization. Given that the noise in the measurement ranged from 5-20 Hz, and the negative and positive control responses were in the range of 0±20 Hz, it is concluded that sensor response to 10 cells/mL was at a signal to noise ration greater than 6. From a measurement perspective, and based on the experiments done to date, it is estimated that a lower detection limit is as low as ~10 cells/mL in beef matrix, or a total cell detection limit of 10 in a sample.

Figure 24:
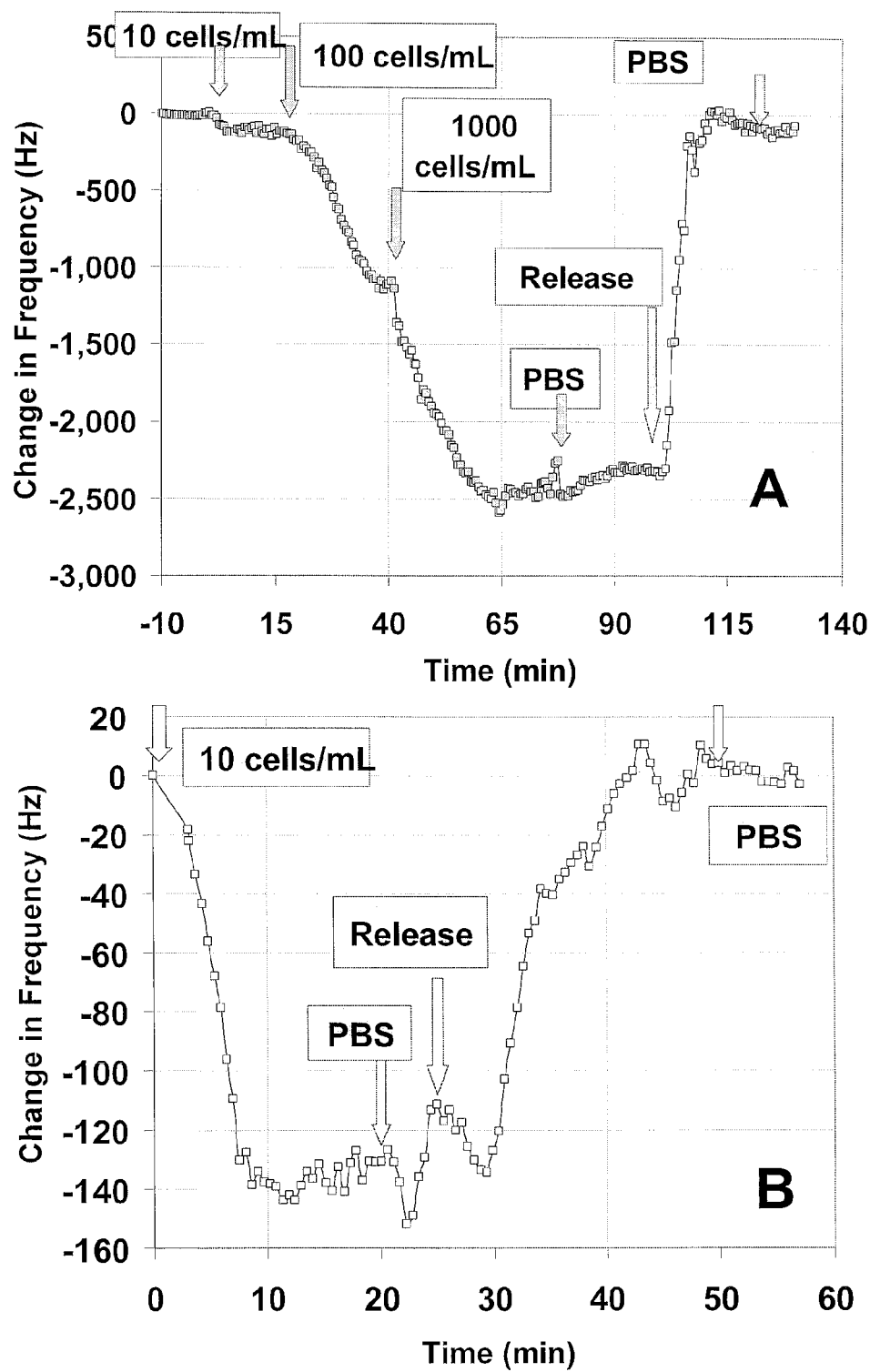
FIG. 24, depicting plots A and B, is an illustration of an example piezoelectric cantilever sensor response to attachment and release of *E. coli* O157:H7 from a sequential addition of 10, 100, and 1,000 cells/mL samples and an illustration of an example piezoelectric cantilever sensor response to attachment and release from the addition of 10 cells/mL sample.

Another method to confirm that sensor response is due to attachment of target pathogen, is to release the bound cells and compare the resulting sensor response. The expectation is the response will be of same magnitude, but opposite in direction. At the conclusion of the experiment given in FIG. 23, a PBS/HCl (pH 2.2) solution was flowed past the sensor surface followed by a PBS flush. The resulting increase in frequency of 2,362 Hz was within 4% of the frequency change due to sample exposure, and is shown in FIG. 24 plot A. FIG. 24, plot A, is an illustration of PEMC sensor response to attachment and release of E. coli O157:H7 from a sequential addition of 10, 100, and 1,000 cells/mL samples. The total frequency change due to the binding and release is 2,456±20 Hz and 2,362±20 Hz, respectively. A second meat sample result is given in FIG. 24 plot B that illustrates the typical release response. Here, attachment of 10 cells/mL of E. coli was followed by a PBS flush, a release, and a second PBS flush. FIG. 24, plot B, is an illustration PEMC sensor response to attachment and release from the addition of 10 cells/mL sample. The total frequency change due to the detection and release is 132±7 Hz and 130±7 Hz, respectively. Negative control response is 27±2 Hz (Not shown). The resultant resonant frequency shift of 130 Hz was within 2% of the pre-antigen resonant frequency value. It is important to note that both the sample flow cell and feed lines were flushed with PBS before and after the E. Coli detection and that the release solution is prepared using PBS. This ensures that the viscosity and density of the fluid surrounding the sensor after detection and prior to release is nearly the same. Additionally, we have previously shown that release of bound antigens using a buffer with pH=2.2 does not result in the release of bound antibody or Protein G. Therefore, the results in FIG. 24 plots A and B show that the change in frequency is indeed due to the release of bound E. coli cells.

In order to obtain visual confirmation of detection, three sensor samples were analyzed in a scanning electron microscope (SEM). Following a detection experiment of 100 cells/mL of ground beef wash the PEMC sensor was rinsed with deionized water and dried at room temperature (~22° C.) for 24 hours. Two additional samples were prepared on antibody-functionalized glass slides exposed to cell concentrations of 10 cells/mL and 1,000 cells/mL, respectively. After exposure, the slides were rinsed with deionized water and dried at room temperature (~22° C.) for 24 hours. SEM examination of approximately fifty fields of 25-35 micron was conducted. The glass slide exposed to 10 and 1,000 cells/mL showed 1 cell and 7 cells, respectively in the evaluated region. Visual inspection of the PEMC sensor used for 100 cells/mL detection showed 2 cells in the inspected fields. In all of the samples exposed, close packing of cells was not observed. It is estimated that the surface covered by cells in each sample was less than 0.2%.

The effect of flow of the medium on the kinetics of binding was analyzed using the approach reported previously. At time close to zero, there are no concentration gradients, and thus diffusion effects are absent. Since the bulk concentration of E. Coli ($C_{b0}$) is known accurately at t=0, limiting the rate analysis to the initial time period was shown as a appropriate approach to determine the kinetics of attachment characterized by the parameter $k_{obs}$, that is, the value of $k_{obs}$, can be determined by analyzing the experimental data in light of the model represented by:

$$\ln\left(\frac{(\Delta f_\infty) - (\Delta f)}{(\Delta f_\infty)}\right) = -k_{obs}\tau \quad (3)$$

Fitting the initial sensor response to E. coli detection presented in FIG. 19 to Equation (3) gives straight lines with excellent correlation coefficients ranging from 0.97 to 0.98 and $k_{obs}$, values of 0.046, 0.052, 0.099, and 0.212 min$^{-1}$ for EC concentrations of 10, 100, 1,000 and 10,000 cells/mL, respectively (figure not shown).

Detection of Ovarian Cancer Antigen

Figure 25:
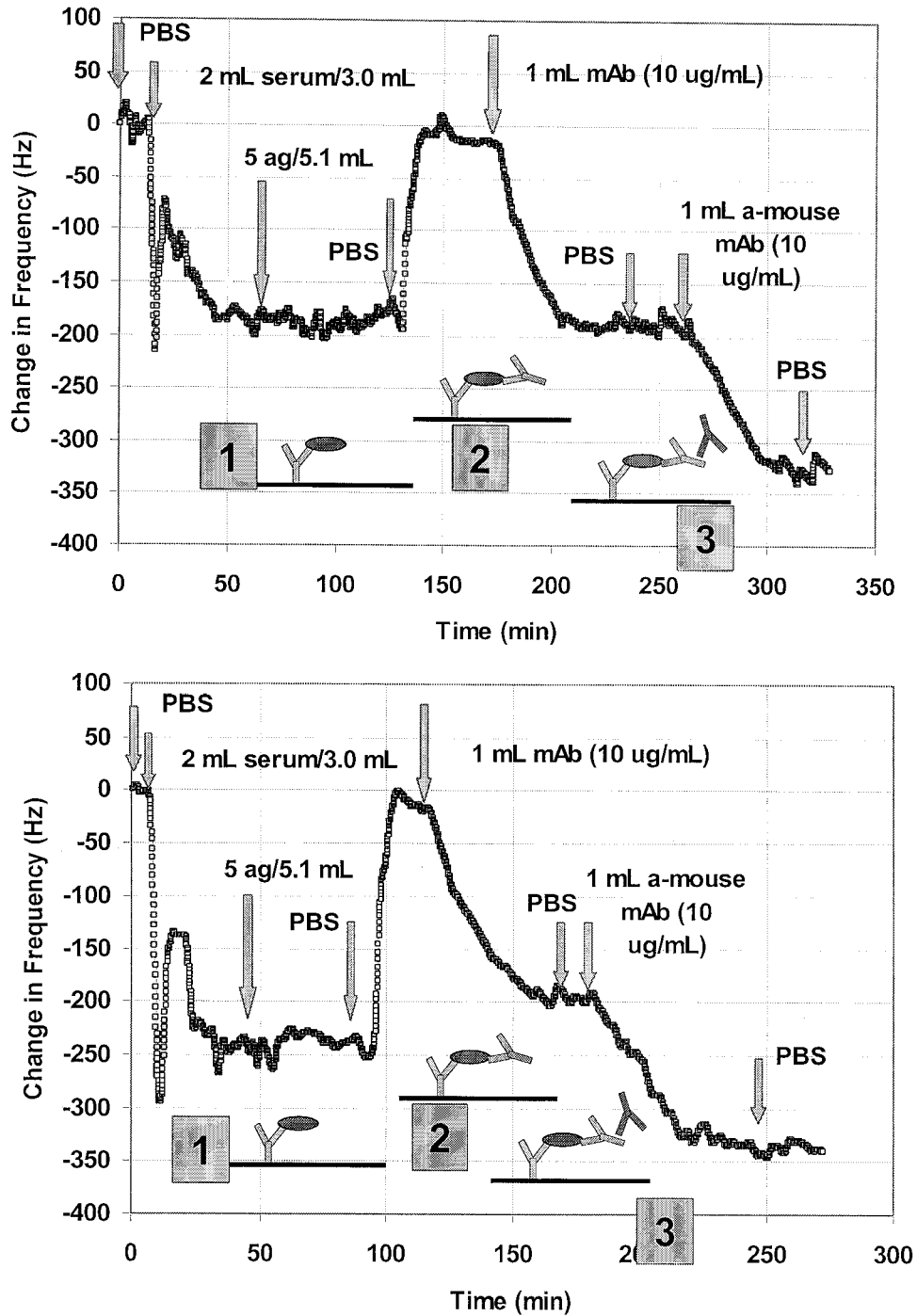
FIG. 25 is an example illustration of the results of detecting ovarian cancer antigen molecules via multiple specific bindings.

Two examples of detection of 100 molecules of ovarian cancer antigen (CA125; 28 kDa) in human serum is show FIG. 25. After stabilizing the cantilever sensor immobilized with an antibody, polyclonal anti-CA125 in phosphate buffered saline solution (PBS; 10 mM), 2 mL human serum was introduced into the flow loop containing 3 mL running buffer. The initial downward response shown in the plots of FIG. 25 is due to higher density serum. As shown, the response stabilizes as the serum mixes with the PBS in the flow loop. To expose the cantilever sensor to the target material, one hundred micro-liters containing 5 attograms of CA125 (100 molecules) was injected into the flow loop in recirculation. As shown, the resulting response was not discernable. The expected binding is illustrated by the illustrations labeled 1. PBS was then introduced to flush the flow loop. To expose the cantilever sensor to an additional antigen, one mL of 10 µg/mL murine monoclonal anti-CA125 was introduced in recirculation. As shown, it caused an upward shift as it attached to the bound CA125 on the sensor. The illustrations labeled 2 depict the anticipated capture. The cantilever sensor was exposed to another type of antibody: goat anti-murine IgG. The goat anti-murine IgG bound to the murine monoclonal anti-CA125. The binding is illustrated by the illustrations labeled 3. The two plots in FIG. 25 indicate that the response is reproducible within ~3%. Variance in 5 experiments was 5.4%. Controls are not shown. None of the antibodies bind to sensor without CA125 exposure. CA125 did not bind to a sensor without an antibody on the sensor. Serum proteins did not adsorb onto bare sensor or sensor prepared with either a poly or monoclonal antibody.

Detection of Staphylococcal Enterotoxin B

Figure 26:
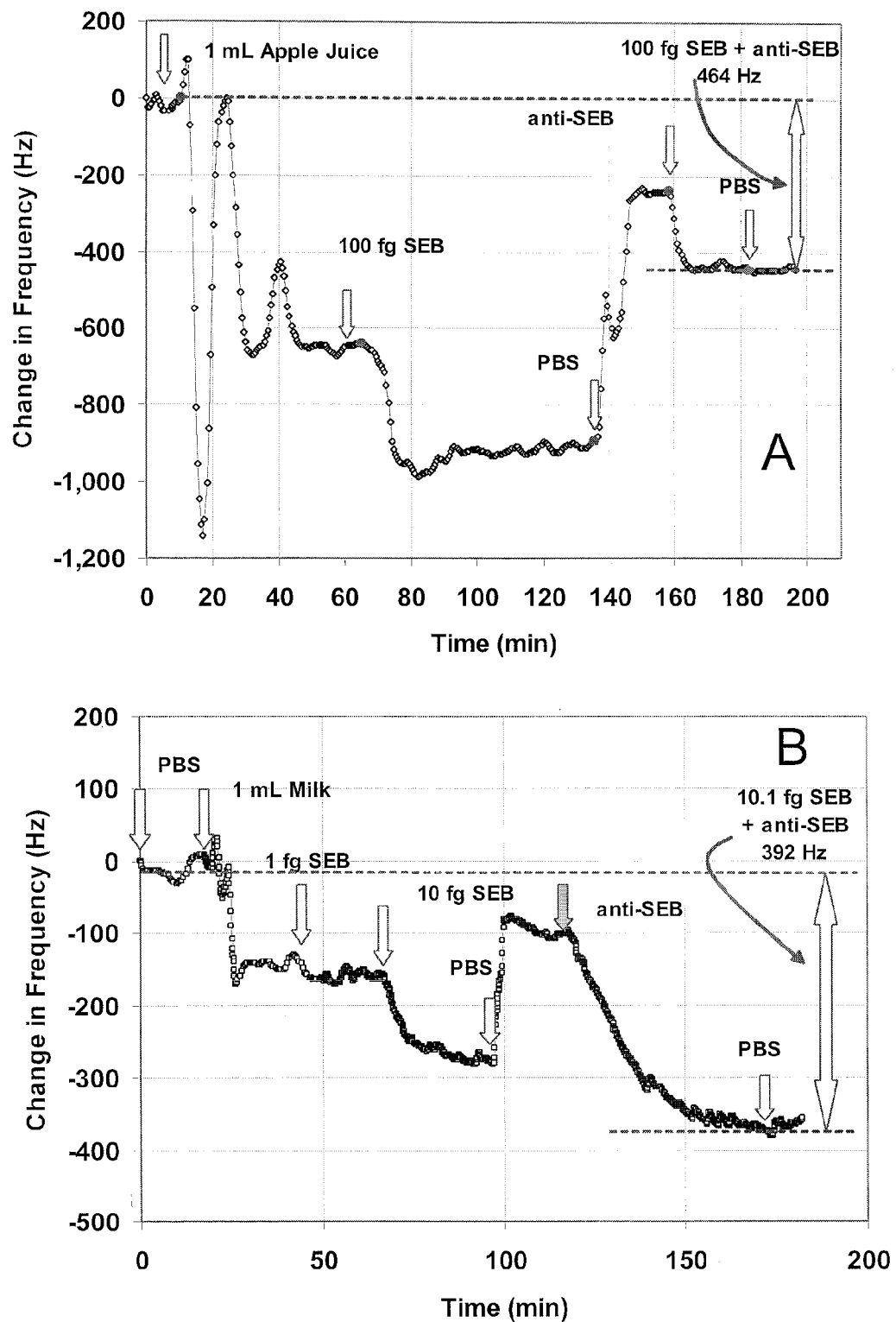
FIG. 26, depicting plots A and B, is an example illustration of the results of detecting staphylococcal enterotoxin B in apple juice and milk via multiple specific bindings.

FIG. 26 depicts two plots of the results of detecting staphylococcal enterotoxin B (SEB) in apple juice and milk. Milk is a complex fluid containing proteins, lipids, sugars, salts and other materials. Apple juice also contains particulate matter small amounts of proteins, carbohydrates, sugars and salts. After stabilizing the antibody-immobilized sensor in running buffer (PBS; 3 mL) one mL of apple juice (plot A) and milk (plot B) was introduced and allowed to mix as the mixture is recirculated. The downward response is due to higher density of both apple juice and milk. In the experiment given in plot A for apple juice, after detection and PBS flush, one mL of 10 µg/mL of polyclonal anti-SEB was pumped into the flow cell in a recirculation mode for 40 minutes. The 100 fg SEB resulted in a frequency decrease of 262±8 Hz (plot A), and the second antibody flow caused a further decrease of 202±10 Hz. The decrease due to binding of antibody to the sensor-bound SEB confirmed that the frequency decrease observed during detection was due to SEB binding to the sensor. If every toxin molecule had an exposed antigenic surface, the expected response would be approximately five times SEB response since mass ratio of antibody to SEB is ~5. For the case in plot A, the response was comparable and such a response suggests that only ~20% of SEB on the surface had a recognizable exposed antigenic site. Since the second antibody attachment was done in buffer, and the mass of antibody for completely coverage the sensor surface is estimated as 1 ng, it is deduced that the availability of limited antigenic sites of SEB is a reasonable explanation for the observed lower response.

A similar confirmation experiment was conducted in milk. After a detection experiment with 10 fg/mL SEB, the flow cell was rinsed with PBS, followed by the introduction of one mL of 10 μg/mL of anti-SEB in recirculation mode for 40 minutes. The attachment of SEB in milk resulted in a frequency decrease of 121±4 Hz (plot. B), and the second antibody run caused a further decrease of 271±5 Hz. Here, the secondary antibody resulted in a two-fold decrease as with SEB attachment. Since these experiments are repeatable well within ±50 Hz, the difference is well beyond experimental error, and one concludes that milk offers a more favorable secondary binding environment compared to apple juice.

Detection Via DNA Hybridization

Figure 27:
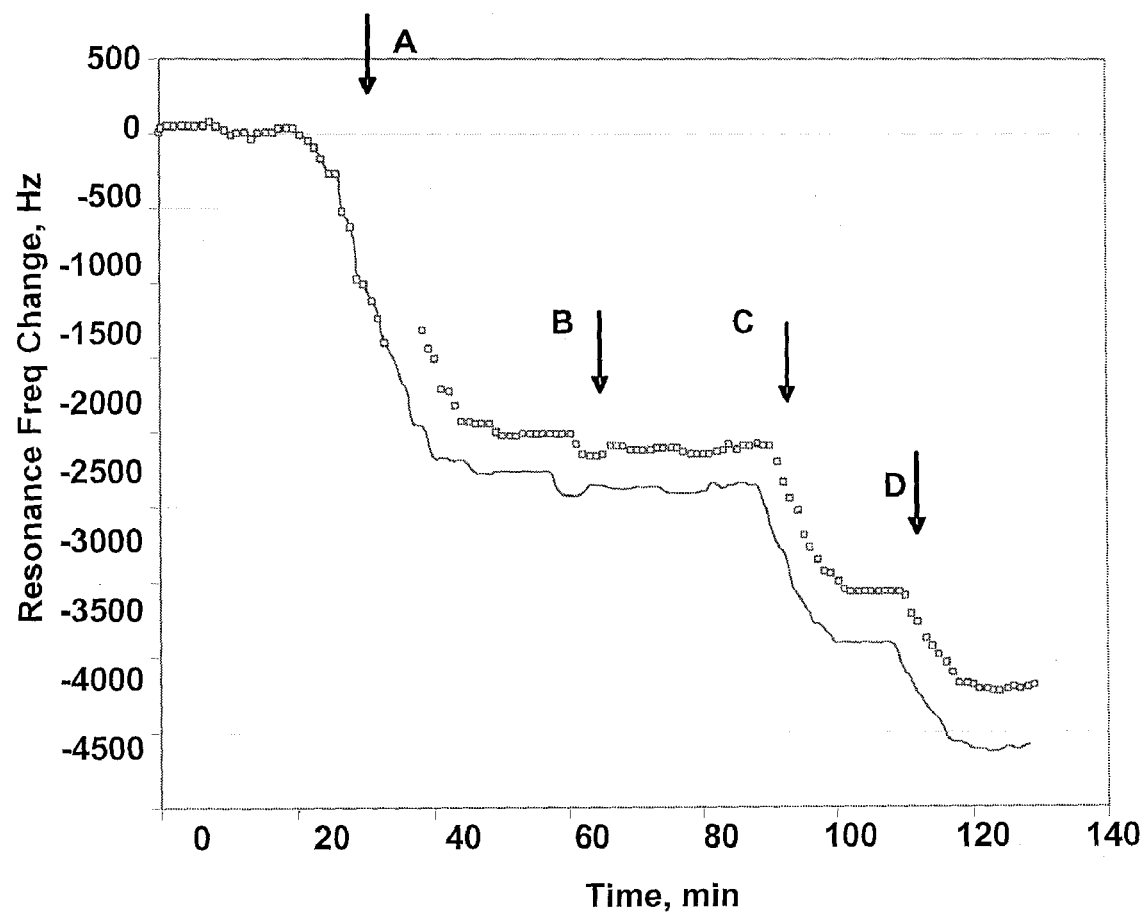
FIG. 27 is a plot illustrating example results of detection of DNA via hybridization of unlabeled DNA.

FIG. 27 is a plot illustrating the addition of mass to a cantilever sensor by hybridizing unlabeled ssDNA to complementary strands that extend from the sensor surface. example results of detection of DNA. A gold-coated cantilever sensor (Resonance Frequency 826 kHz) was immobilized with a thiolated single strand DNA (ssDNA) with an 18-mer sequence HS—(CH$_2$)$_6$-5'CTC CAGGG CCAGG CGGCG3' (SEQ ID NO:1) by introducing at t=20 min (labeled A) and circulated in the flow apparatus prepared in TRIS-EDTA buffer+50 mM NaCL at 10 pM and 3 mL sample. The immobilization caused a shift down of nearly 2200 Hz in resonance frequency. After reaching equilibrium, 1.5 mL 1 μM mercaptohexanol (labeled B) was circulated to orient the immobilized ssDNA and a small resonance shift down is noted. Subsequently, 2 mL of 1 pM solution of freshly denatured 288-mer section of APP gene (SEQ ID NO: 2)
(5'
CATTTCCAGGAGAAAGTGGAATCTTTGGAA

CAGGAAGCAGCCAACGAGAGACAGCAGCTG

GTGGAGACACACATGGCCAGAGTGGAAGCC

ATGCTCAATGACCGCCGCCGCCTGGCCCTG

GAGAACTACATCACCGCTCTGCAGGCTGTT

CCTCCTCGGCCTCGTCACGTGTTCAATATG

CTAAAGAAGTATGTCCGCGCAGAACAGAAG

GACAGACAGCACACCCTAAAGCATTTCGAG

CATGTGCGCATGGTGGATCCCAAGAAAGCC

GCTCAGATCCGGTCCCAG

3')

was circulated (labeled C) which immediately hybridized causing a shift down of 1055 Hz. After reaching steady state, the hybridization was confirmed by introducing and circulating (labeled D) 3 mL of 1 pM of 20-mer strand complementary to APP gene that hybridizes to position 54 to 74 (in bold and double underlined above) in APP gene. Position count is from 5' to 3' position. Note that the probe hybridized to position indicated in bold and underlined above. The response 698 Hz is because of addition of mass due to hybridization in position 54 to 74. Note in the above experiment the probe immobilized on the sensor hybridizes between position 105 and 124 on APP gene. The ratio of second hybridization to the first one is =698/1055=0.66.

Detection Via DNA Extension Using Polymerase

Figure 28:
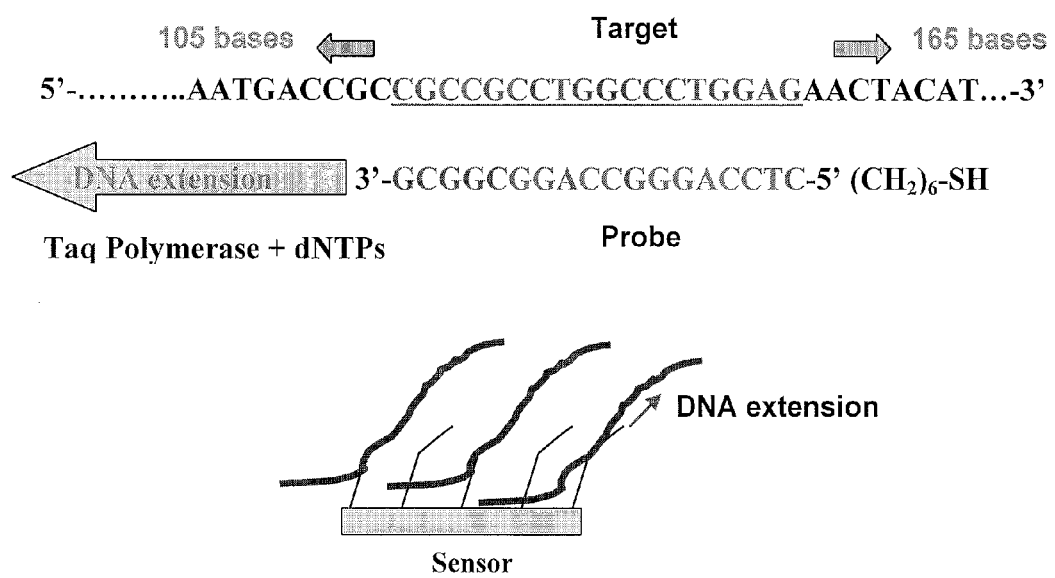
FIG. 28 is an illustration of an example of DNA extension using polymerase to increase mass on a cantilever sensor. (SEQ ID NOS: 4 and 5)

Increased detection sensitivity was achieved by adding mass by reaction. As shown in FIG. 28, a probe contains 18 bases complementary to 18 bases on an amyloid precursor protein (APP) gene. 105 and 165 bases are on either side of the hybridization section as depicted in FIG. 28. The 3' end of the probe thus acts as starting point for DNA polymerization where Taq DNA Polymerase catalyzes incorporation of bases complementary to the template (target strand). Target and probe strands (respectively labeled in FIG. 28) are not depicted to scale. The arrow pointing away from the sensor in FIG. 28 indicates the direction of DNA extension. After the occurrence of extension, 20 base ssDNA complementary to 54-74 on APP did not give a hybridization response, thus indicating that DNA extension did take place in the direction.

The test involved a probe sequence immobilized on a cantilever sensor surface comprising 18-mer sequence HS—(CH$_2$)$_6$-5'CTC CAGGG CCAGG CGGCG3' (SEQ ID NO:1) which hybridizes with position 105 to 124 in the APP gene. The probe that would hybridize to the complementary APP gene, and its complement HS—(CH$_2$)$_6$-5'CGCCGCCTG-GCCCTGGAG3' (SEQ ID NO:3) was also immobilized on the sensor. FIG. 28 shows the relative position of the sense strand. Once the APP gene is hybridized there are 105 bases towards 5' end of the target (APP gene) and 165 bases towards the 3' end. A Taq polymerase was used which extended the immobilized probe in 3→5 direction such that a maximum of 105 bases is added as shown in FIG. 28. The probe immobilized on the sensor comprises a sequence complementary to both of the denatured APP dsDNA. A freshly prepared 2 mL probe comprising both sequences in a 1:1 mole ratio at a concentration of 10 pM was flowed through the sensor after equilibrating the sensor in TE buffer.

Figure 29:
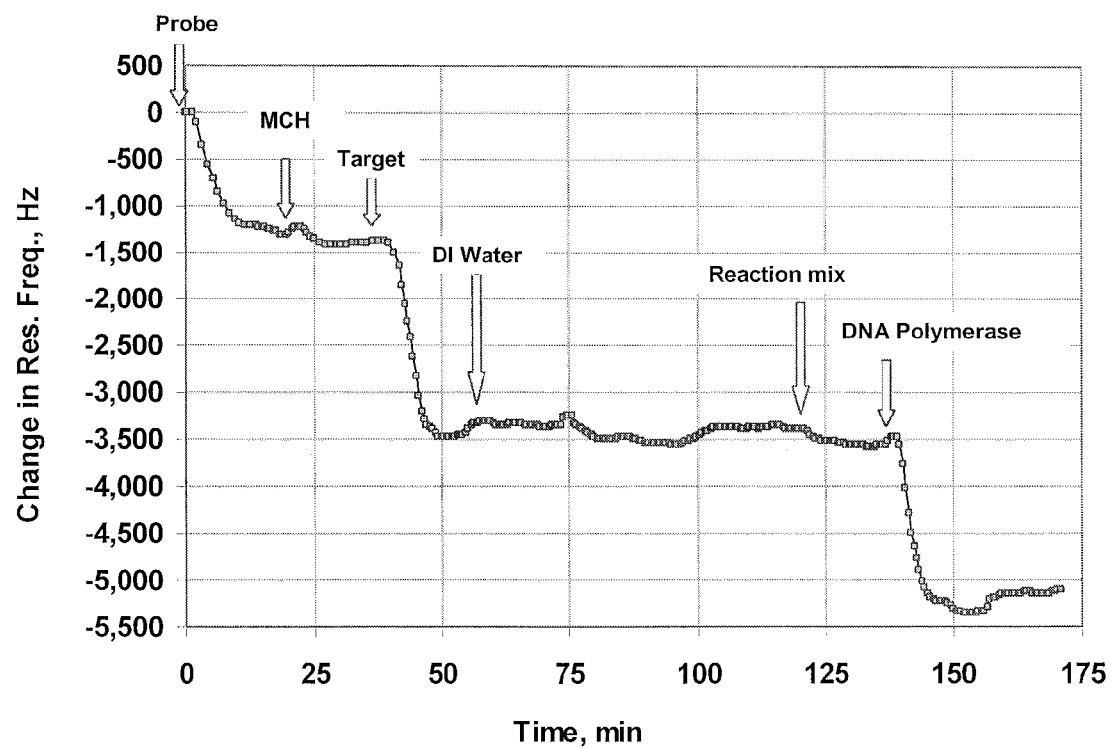
FIG. 29 is an example illustrative plot of the change in resonance frequency due to a change in mass resulting from DNA extension using polymerase.

As shown in FIG. 29, the flow of probe solution resulted in a decrease of 1,360 Hz. At t=23 minute, the flow was then switched to 2 mL of freshly prepared 1 μM MCH solution in TE buffer to fill unoccupied Au <111> sites and to remove any non-specifically attached probe strands. At t=40 min, 2 mL of 1 pM freshly denatured APP target in TE buffer was introduced. A change in resonance frequency, resulting in a decrease of 2,095 Hz in 11.1 min occurred. At t=55 min, nuclease free DI water was pumped in to purge the system of buffer and DNA. When DI water initially entered the flow-cell chamber, there was a slight increase in resonance frequency (150 Hz) and is concluded to be due to a small temperature change in the flow-cell (~0.2° C.). However, during the flow of DI water for 67 minutes (33.5 mL), the noise level was ±150 Hz but no overall change in resonance frequency occurred. At t=120 min, a freshly prepared 1.5 mL reaction mixture containing 150 μL 10× Taq buffer, 30 μL 10 mM dNTP with remaining DI water was flowed in. As seen in FIG. 29, as soon as the mix entered the flow-cell, there was a decrease of −116±15 Hz within the first 5 minutes. It took approximately 4-5 minutes for the new analyte to completely replace the previous one in the flow cell. The rapid change in resonance frequency occurred with maximum reaching within the first 5 minutes indicates that this small change in resonance frequency is due to the density difference of the reaction mixture. Solution of dNTP in Taq buffer is denser than DI water. At t=140 min, 25 μL of Taq DNA polymerase is added to the circulating reaction mix and mixed thoroughly with a pipette. As the polymerase mixed in the resonance frequency rapidly decreased progressively resulting in 1,838±36 Hz in 11.4 minutes. This decrease in resonance frequency is due to the addition of mass on the sensor surface. When DNA Taq polymerase was not present in the reaction mix, there was no significant change in the resonance frequency; however, the presence of polymerase catalyzed the reaction of nucleotide addition, thus extending the probe to form double stranded DNA. The maximum change occurred in 11.4 minutes. Taq polymerase can add 60 nt/s at its optimum temperature. Good catalytic activity was observed at 70-75° C. At the chosen temperature of 46.2±0.1° C., the activity was lower by <5%. It is estimated that the reaction can add up to a maximum of approximately 6 nt/s. Ideally, this should take only ~18 seconds to extend all hybridized target to maximum once the chamber containing the sensor is filled with reaction mixture and the polymerase. The fact that it takes 5-6 minutes suggests that the DNA extension is indeed very slow.

Figure 30:
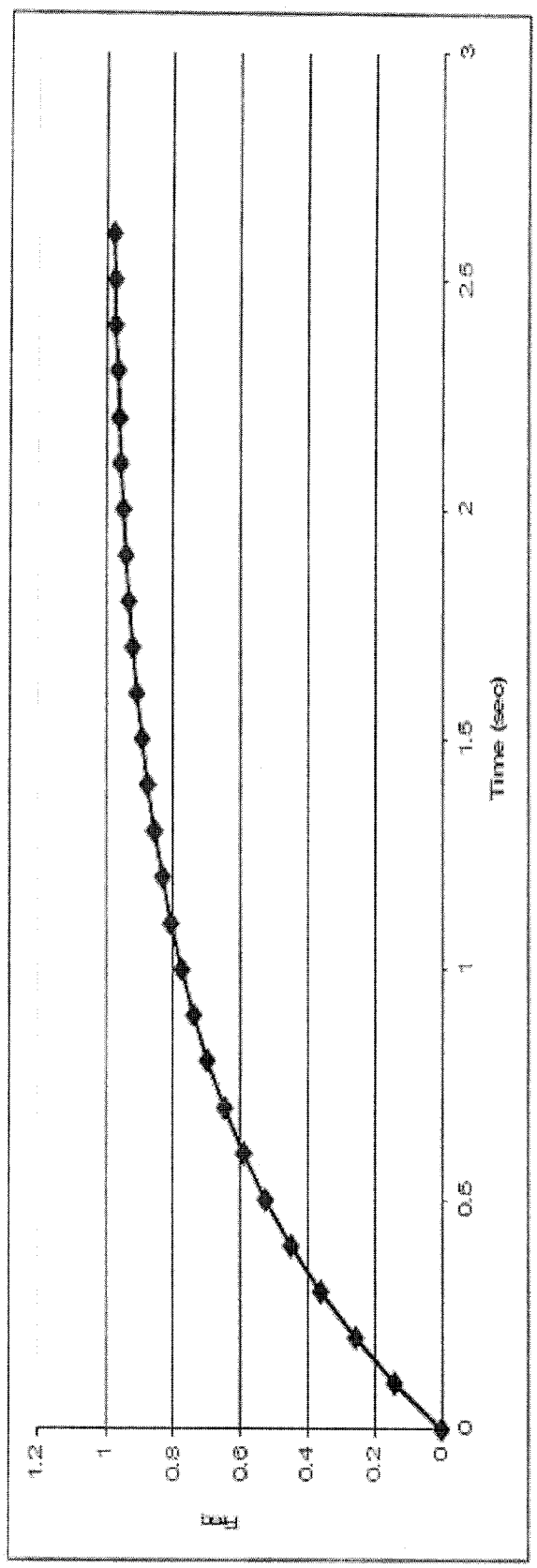
FIG. 30 is an example illustrative plot of the change in resonance frequency due to a change in mass, which depicts the kinetics of equilibrium binding between recognition molecules and analytes.

FIG. 30 is an example illustrative plot of the change in resonance frequency due to a change in mass, which depicts the kinetics of equilibrium binding between recognition molecules and analytes. As depicted in FIG. 30, the change in resonance frequency over time reflects the kinetics of the binding reaction between recognition molecules and analytes, and/or recognition molecules and recognition molecules. The rate at which the binding reactions reaches equilibrium is utilizable to quantify characteristics of the binding partners, such as for example, the affinity of the binding partners for one another, which in turn facilitates identification of binding partners.

Figure 31:
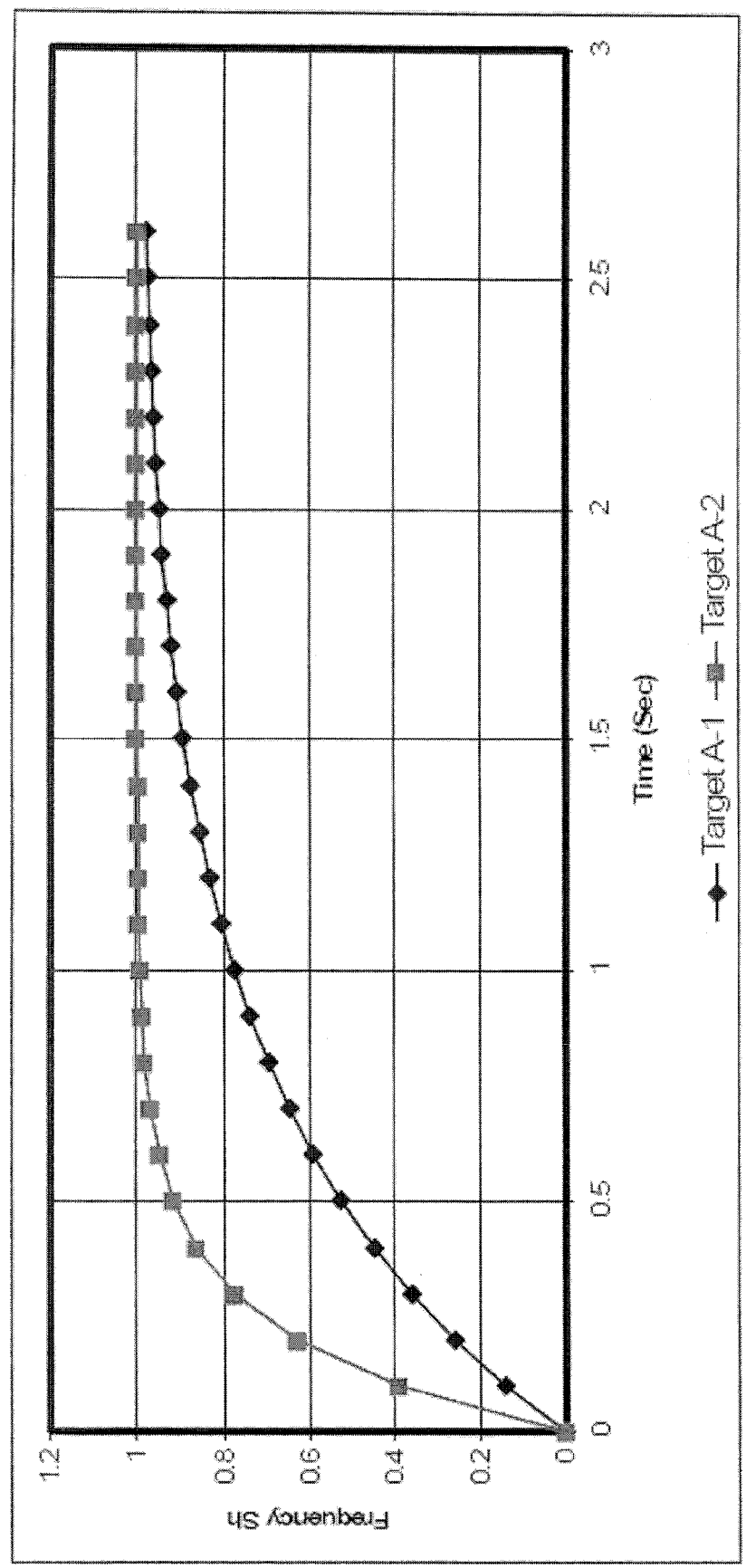
FIG. 31 is an example illustrative plot of the change in resonance frequency due to a change in mass, which depicts the kinetics of equilibrium binding between recognition molecules and analyte A-1 (squares) and recognition molecules and analyte A-2 (diamonds).

FIG. 31 is an example illustrative plot of the change in resonance frequency due to a change in mass, which depicts the kinetics of equilibrium binding between recognition molecules and analyte A-1 (squares) and recognition molecules and analyte A-2 (diamonds). FIG. 31 illustrates that the time to reach equilibrium is different for different analytes and thus is utilizable to determine characteristics of an analyte.

Figure 32:
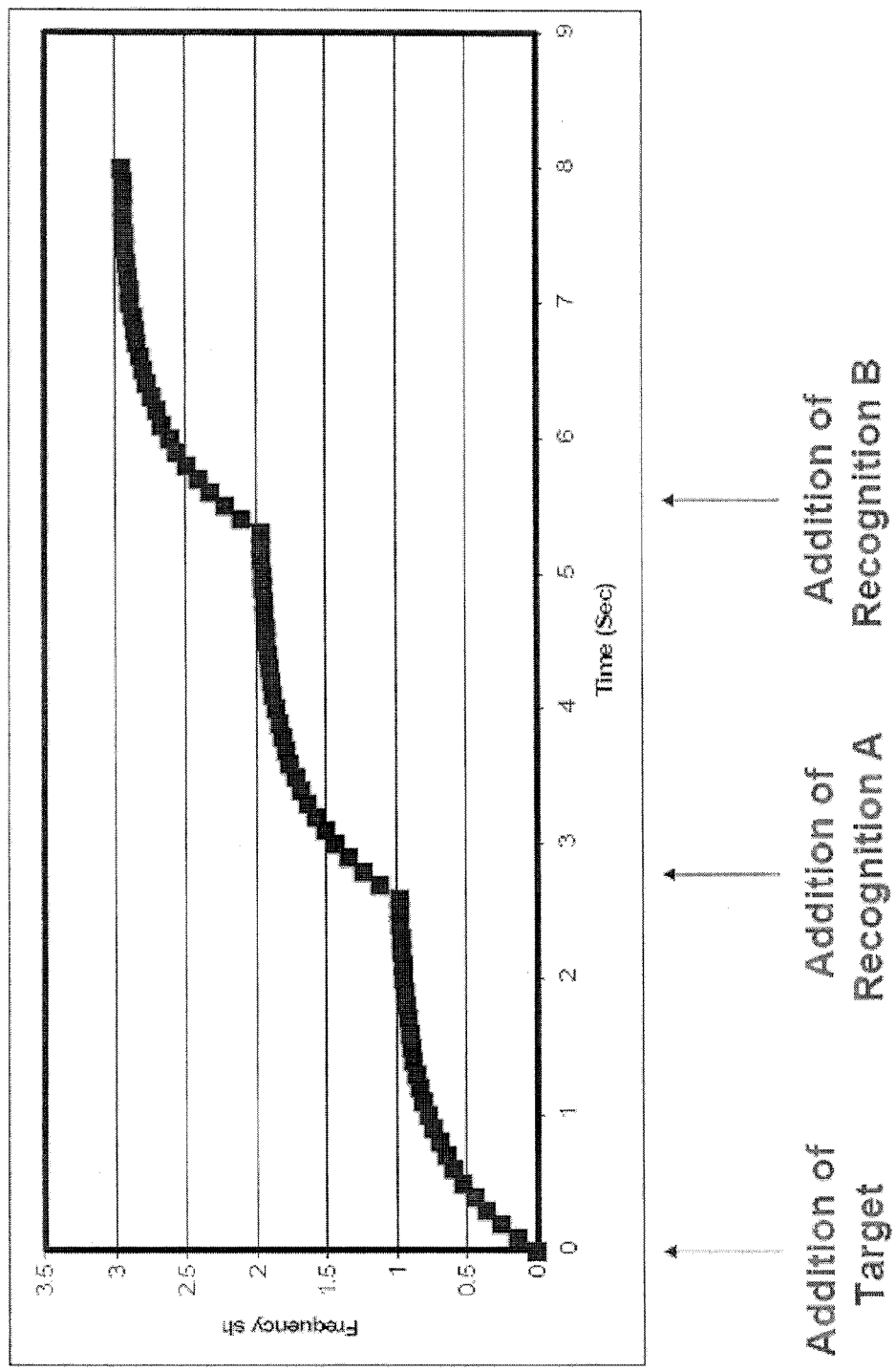
FIG. 32 is an example illustrative plot of the change in resonance frequency due to a change in mass depicting the kinetics of equilibrium binding of sequential addition of analytes and recognition molecules.

FIG. 32 is an example illustrative plot of the change in resonance frequency due to a change in mass depicting the kinetics of equilibrium binding of sequential addition of analytes and recognition molecules. At time 0, target analytes bind to recognition molecules. Upon reaching equilibrium, recognition molecules A are added, bind to target analytes, and reach equilibrium. After reaching equilibrium recognition molecules B are added, bind to recognition molecules A, and reach equilibrium.

While illustrative embodiments of enhanced sensitivity of a cantilever sensor via a plurality of specific bindings have been described herein, it is to be understood that other similar embodiments can be used or modifications and additions can be made to the described embodiment of enhanced sensitivity of a cantilever sensor via a plurality of specific bindings without deviating therefrom. Therefore, enhanced sensitivity of a cantilever sensor via a plurality of specific bindings should not be limited to any single embodiment, but rather should be construed in breadth and scope in accordance with the appended claims.

What is claimed:

1. A method for detecting an analyte via a sensor configured to sense mass, the method comprising:
immobilizing first recognition molecules to a surface of the sensor, wherein the first recognition molecules are bindable to the analyte, the sensor comprising:
a piezoelectric layer comprising a proximate end and a distal end;
a non-piezoelectric layer comprising a proximate end and a distal end, wherein at least a portion of the piezoelectric layer is coupled to at least a portion of the non-piezoelectric layer such that the piezoelectric layer and the non-piezoelectric layer are not coextensive;
a base portion coupled to the proximate end of the piezoelectric layer, wherein the base portion is not attached to the proximate end of the non-piezoelectric layer; and
electrodes operatively associated with the piezoelectric layer;
via a first exposure, exposing the sensor, having the first recognition molecules immobilized thereon, to the analyte;
via a second exposure subsequent to the first exposure, exposing the sensor to second recognition molecules; and
determining an amount of total mass of material accumulated on the sensor, wherein the total mass comprises an amount of mass accumulated on the sensor resulting from the first exposure and the second exposure; and
determining if analyte has been detected in accordance with the determined amount of total mass.

2. The method in accordance with claim 1, wherein the total mass comprises:
a mass of the analyte bound to the first recognition molecules via the first exposure; and
a mass of the second recognition molecules bound to the analyte via the second exposure.

3. The method in accordance with claim 1, further comprising measuring the binding kinetics of the analyte to the immobilized recognition molecules by the rate of change in resonance frequency over time, wherein equilibrium is achieved when the rate of change in resonance frequency versus time is zero.

4. The method in accordance with claim 3, further comprising determining a characteristic of the analyte in accordance with the measured binding kinetics.

5. The method in accordance with claim 1, further comprising, subsequent to the second exposure, sequentially performing at least one additional exposure, wherein:
during each at least one additional exposure, the sensor is exposed to a respective type of recognition molecule, and
each respective type of recognition molecule is bindable to a type of recognition molecule of a previous exposure.

6. The method in accordance with claim 5, further comprising measuring the binding kinetics of the additional exposures by measuring the rate of change in resonance frequency over time after additional exposures, wherein equilibrium is achieved where the rate of change in resonance frequency versus time is zero.

7. The method in accordance with claim 1 wherein:
the first recognition molecules comprise a first antibody;
the second recognition molecules comprise a second antibody; and
the first antibody is the same as the second antibody.

8. The method in accordance with claim 1, wherein:
the first recognition molecules comprise a first antibody;
the second recognition molecules comprise a second antibody; and
the first antibody differs from the second antibody.

9. The method in accordance with claim 1, wherein the second recognition molecules comprise at least one unlabeled antibody.

10. The method in accordance with claim 1, wherein:
the second recognition molecules comprise at least one labeled antibody; and
the at least one labeled antibody comprises at least one mass increasing component.

11. The method in accordance with claim 10, wherein the mass increasing component comprises a dendrimer.

12. The method in accordance with claim 1, wherein:
the first recognition molecules comprise an antibody; and
the analyte comprises an antigen.

13. The method in accordance with claim 1, wherein:
the analyte comprise first DNA strands;
the second recognition molecules comprise second DNA strands complementary to the first DNA strands.

14. The method in accordance with claim 13, further comprising utilizing a polymerase to facilitate binding the first DNA strands to the second DNA strands.

15. The method in accordance with claim 1, wherein the second recognition molecules comprise at least one DNA strand.

16. The method in accordance with claim 1, wherein the second recognition molecules comprise at least one DNA strand comprising a mass increasing component.

17. The method in accordance with claim 16, wherein the mass increasing component is a dendrimer.

18. The method in accordance with claim 1, wherein the second recognition molecules further comprise a label for identifying the analyte.

19. The method in accordance with claim 1, wherein the second recognition molecules comprise at least one monoclonal antibody.

20. The method in accordance with claim 1, wherein the second recognition molecules comprise at least one polyclonal antibody.

21. The method in accordance with claim 1, wherein the analyte comprises at least one of a bioterrorism agent, a food-borne pathogen, a water pathogen, a cell type in a body fluids, a biomarker in a body fluid, an indication of an explosive material, an airborne toxin, a waterborne toxin, a biological entity, a protein, a lipoprotein, DNA, and RNA.

22. The method in accordance with claim 1, further comprising:
prior to the first exposure, measuring, via the electrodes, a resonance frequency of the sensor to obtain a first measurement;
subsequent to the second exposure, measuring, via the electrodes, a resonance frequency of the sensor to obtain a second measurement;
comparing the first measurement to the second measurement;
if the first measurement differs from the second measurement, determining that an analyte is detected.

* * * * *